US011944498B2

(12) United States Patent
Tashiro

(10) Patent No.: US 11,944,498 B2
(45) Date of Patent: *Apr. 2, 2024

(54) ULTRASOUND DIAGNOSTIC SYSTEM AND METHOD OF CONTROLLING ULTRASOUND DIAGNOSTIC SYSTEM

(71) Applicant: FUJIFILM Corporation, Tokyo (JP)

(72) Inventor: Rika Tashiro, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/902,499

(22) Filed: Sep. 2, 2022

(65) Prior Publication Data

US 2022/0409179 A1   Dec. 29, 2022

Related U.S. Application Data

(60) Division of application No. 16/290,539, filed on Mar. 1, 2019, now Pat. No. 11,478,223, which is a
(Continued)

(30) Foreign Application Priority Data

Sep. 12, 2016 (JP) .................... 2016-177885

(51) Int. Cl.
*A61B 8/08* (2006.01)
*A61B 8/00* (2006.01)
(Continued)

(52) U.S. Cl.
CPC ............ *A61B 8/463* (2013.01); *A61B 8/14* (2013.01); *A61B 8/464* (2013.01); *A61B 8/465* (2013.01);
(Continued)

(58) Field of Classification Search
CPC .......... A61B 8/463; A61B 8/14; A61B 8/464; A61B 8/465; A61B 8/467; A61B 8/5207;
(Continued)

(56) References Cited

U.S. PATENT DOCUMENTS

2004/0068423 A1   4/2004 Shaw
2004/0193053 A1   9/2004 Kato
(Continued)

FOREIGN PATENT DOCUMENTS

| CN | 1890579 A | 1/2007 |
|---|---|---|
| CN | 101066210 A | 11/2007 |

(Continued)

OTHER PUBLICATIONS

Chinese Office Action and Search Report, dated Mar. 2, 2021, for corresponding Chinese Application No. 201780055500.7, with an English translation of the Chinese Office Action.
(Continued)

*Primary Examiner* — Baisakhi Roy
*Assistant Examiner* — Kaitlyn E Sebastian
(74) *Attorney, Agent, or Firm* — Birch, Stewart, Kolasch & Birch, LLP

(57) ABSTRACT

In an ultrasound diagnostic system, in a case where a routine test in which a plurality of parts of a subject are sequentially subjected to ultrasound diagnosis in accordance with a determined procedure is performed and in a case where information on the subject is input from an input unit, a workstation-side control unit makes a workstation-side display unit perform a second display in which one past image and a current image including an ultrasound image newly created in an ultrasound diagnostic device with respect to a part corresponding to the one past image are displayed side by side on a past image region and a current image region adjacent to each other, in an arrangement order of a plurality
(Continued)

of past images in a past routine test of the subject stored in the storage unit.

19 Claims, 11 Drawing Sheets

Related U.S. Application Data continuation of application No. PCT/JP2017/032316, filed on Sep. 7, 2017.

(51) Int. Cl.
| | | |
|---|---|---|
| *A61B 8/14* | (2006.01) | |
| *G01S 7/52* | (2006.01) | |
| *G16H 15/00* | (2018.01) | |
| *G16H 40/63* | (2018.01) | |

(52) U.S. Cl.
CPC ............ *A61B 8/467* (2013.01); *A61B 8/5207* (2013.01); *A61B 8/54* (2013.01); *G01S 7/52053* (2013.01); *A61B 8/4416* (2013.01); *G16H 15/00* (2018.01); *G16H 40/63* (2018.01)

(58) Field of Classification Search
CPC ..... A61B 8/54; A61B 8/4416; G01S 7/52053; G16H 15/00; G16H 40/63; G16H 50/20; G16H 30/20
See application file for complete search history.

(56) References Cited

U.S. PATENT DOCUMENTS

| | | | |
|---|---|---|---|
| 2005/0177391 A1 | 8/2005 | Shimizu et al. | |
| 2005/0259116 A1 | 11/2005 | Araoka | |
| 2007/0055161 A1 | 3/2007 | Garg et al. | |
| 2007/0259158 A1 | 11/2007 | Friedman et al. | |
| 2008/0193004 A1 | 8/2008 | Mine | |
| 2009/0080744 A1 | 3/2009 | Sagawa | |
| 2012/0108960 A1* | 5/2012 | Halmann | A61B 8/5292 715/810 |
| 2013/0335441 A1 | 12/2013 | Zalev et al. | |
| 2014/0143710 A1 | 5/2014 | Zhao et al. | |
| 2015/0164475 A1 | 6/2015 | Kuga et al. | |
| 2015/0164479 A1 | 6/2015 | Toji | |
| 2015/0209013 A1 | 7/2015 | Tsymbalenko | |
| 2015/0257738 A1* | 9/2015 | Kim | A61B 8/523 600/440 |
| 2015/0262553 A1 | 9/2015 | Nam et al. | |
| 2015/0305718 A1 | 10/2015 | Ogasawara | |
| 2015/0335303 A1 | 11/2015 | Chandelier et al. | |
| 2016/0206291 A1* | 7/2016 | Yang | A61B 8/5253 |
| 2017/0038951 A1* | 2/2017 | Reicher | G06F 16/583 |
| 2017/0351843 A1 | 12/2017 | Tajima et al. | |

FOREIGN PATENT DOCUMENTS

| | | |
|---|---|---|
| CN | 104602610 A | 5/2015 |
| CN | 104905812 A | 9/2015 |
| CN | 104969265 A | 10/2015 |
| EP | 2898832 A1 | 7/2015 |
| JP | 2001-353148 A | 12/2001 |
| JP | 2004-290404 A | 10/2004 |
| JP | 2008-188163 A | 8/2008 |
| JP | 2014-158693 A | 9/2014 |
| JP | 2015-198807 A | 11/2015 |
| JP | 5982461 B2 | 8/2016 |

OTHER PUBLICATIONS

Extended European Search Report, dated Aug. 27, 2019, for corresponding European Application No. 17848848.2.
Final Office Action issued in U.S. Appl. No. 16/290,539, dated Oct. 1, 2021.
International Preliminary Report on Patentability and Written Opinion (Forms PCT/IB/326, PCT/IB/373, and PCT/ISA/237) for International Application No. PCT/JP2017/032316, dated Mar. 21, 2019, with English translation.
International Search Report (Forms PCT/ISA/210) for International Application No. PCT/JP2017/032316, dated Dec. 12, 2017, with English translation.
Non-Final Office Action issued in U.S. Appl. No. 16/290,539, dated Jan. 28, 2022.
Non-Final Office Action issued in U.S. Appl. No. 16/290,539, dated May 28, 2021.
Notice of Allowance issued in U.S. Appl. No. 16/290,539, dated Jul. 12, 2022.
Notice of Allowance issued in U.S. Appl. No. 16/290,539, dated Jun. 7, 2022.
Restriction/Election Requirement issued in U.S. Appl. No. 16/290,539, dated Dec. 16, 2020.

* cited by examiner

ULTRASOUND DIAGNOSTIC SYSTEM AND METHOD OF CONTROLLING ULTRASOUND DIAGNOSTIC SYSTEM

CROSS-REFERENCE TO RELATED APPLICATIONS

This application is a Divisional of U.S. application Ser. No. 16/290,539 filed on Mar. 1, 2019, which is a Continuation of PCT International Application No. PCT/JP2017/032316 filed on Sep. 7, 2017, which claims priority under 35 U.S.C. § 119(a) to Japanese Patent Application No. 2016-177885 filed on Sep. 12, 2016. The above applications are hereby expressly incorporated by reference, in their entirety, into the present application.

BACKGROUND OF THE INVENTION

1. Field of the Invention

The present invention relates to an ultrasound diagnostic system and a method of controlling an ultrasound diagnostic system, and particularly, to an ultrasound diagnostic system in which an ultrasound diagnostic device and a workstation are connected to each other and that displays diagnostic results in the ultrasound diagnostic device on the workstation at any time, and a method of controlling the ultrasound diagnostic system.

2. Description of the Related Art

Ultrasound diagnostic devices have been known as devices for obtaining an image inside a subject by applying an array transducer to a subject. General ultrasound diagnostic devices transmit an ultrasound beam toward the inside of the subject from the array transducer in which a plurality of elements were arranged, and receive the ultrasound echoes from the subject in the array transducer to acquire element data. Moreover, the ultrasound diagnostic devices electrically process the obtained element data to obtain an ultrasound image of a relevant part of the subject concerned.

In a test performed using such ultrasound diagnostic devices, operators, such as a doctor and an engineer, often perform the test while checking an ultrasound image displayed on each ultrasound diagnostic device or the like. For that reason, for the purpose of efficient testing, various devices have been tried in the image display in a display unit of the ultrasound diagnostic device (refer to JP2008-188163A, JP2004-290404A, and JP2015-198807A).

JP2008-188163A discloses an ultrasound diagnostic device connected to a medical image diagnostic device and a medical image server via a network. The ultrasound diagnostic device has a display unit, a display control unit that performs display control for the display unit, a control unit that controls the display control unit, and a reference image list management unit that generates a list indicating saved locations of medical image data acquired in the past. The ultrasound diagnostic device generates a reference image list indicating a list of medical image data preselected by an operator in advance, and selects a desired medical image to display the desired medical image in contrast with a current ultrasound image in a case where the display unit of the ultrasound diagnostic device is made to display medical images. Additionally, in a case where testing and treatment are performed, it is possible to make the display unit of the ultrasound diagnostic device display the desired medical image at a desired timing.

JP2004-290404A discloses an ultrasound diagnostic device having a display unit, a display control unit that creates image data from ultrasound image signals, a data storage unit, and an interface unit for connection to a server via an external network. The ultrasound diagnostic device reads a reference image captured in the past and its scanning conditions that are stored in an ultrasound diagnostic device body or a server, and sets the scanning conditions to capture an ultrasound image. Moreover, the ultrasound diagnostic device displays the captured ultrasound image and the reference image side by side in the display unit.

JP2015-198807A discloses an ultrasound diagnostic device that sets one reference image from a plurality of ultrasound images, and makes a display unit display a reference image, which is a real-time ultrasound image received from an ultrasound probe, and a comparison image, which is a past ultrasound image, side by side. Additionally, the ultrasound diagnostic device body can display conditions of the comparison image in accordance with display conditions of the reference image by a control unit.

SUMMARY OF THE INVENTION

Meanwhile, in general ultrasound diagnosis, in order to check the part of the subject to be imaged in the ultrasound diagnosis and adjust image conditions according to the state of the subject, a screening test in which a plurality of diagnosis parts of the subject are simply observed is often performed prior to a routine test in which the plurality of parts of the subject are sequentially subjected to the ultrasound diagnosis in accordance with a determined procedure. It is preferable that such a screening test is performed while checking ultrasound images that correspond to the part of the subject subjected to the ultrasound diagnosis and are captured in the past, particularly, a list of the past ultrasound images. In the technique disclosed in JP2008-188163A, the list of the ultrasound images captured in the past is displayed on the display unit of the ultrasound diagnostic device simultaneously with an ultrasound image under testing. For that reason, in the display unit of the ultrasound diagnostic device, the list of the ultrasound images captured in the past is displayed to be smaller, and a display region for the ultrasound image under testing is narrow. Therefore, there is a problem that it is difficult to perform the screening test while checking the list of the ultrasound images captured in the past.

Additionally, in the techniques disclosed in JP2004-290404A and JP2015-198807A, the ultrasound images captured in the past are not displayed as a list in the display unit of the ultrasound diagnostic device, an external display device, or the like. For that reason, there is a problem that it is difficult to perform the screening test while checking the ultrasound images that correspond to the part subjected to the ultrasound diagnosis and are captured in the past.

Additionally, in the techniques disclosed in JP2008-188163A, JP2004-290404A, and JP2015-198807A, the ultrasound images captured in the past and the ultrasound image under diagnosis are comparatively displayed only on the display unit of each ultrasound diagnostic device. However, many of the display units built in the ultrasound diagnostic devices are small, and in a case where both of the past ultrasound images and the ultrasound image under diagnosis are displayed on the display unit of the ultrasound diagnostic device, the display region for the ultrasound image under current diagnosis is displayed to be smaller. For that reason, there is a problem that the operator cannot easily check the ultrasound image under current diagnosis.

An object of the invention is to solve the above related-art problems and provide an ultrasound diagnostic system and a method of controlling the ultrasound diagnostic system in which an operator can perform a screening test while checking list display of past diagnostic images of a subject and the operator can easily check an ultrasound image under current diagnosis during the ultrasound diagnosis.

In order to achieve the above object, the ultrasound diagnostic system of the embodiment of the invention is an ultrasound diagnostic system including an ultrasound diagnostic device that transmits an ultrasound beam toward a subject from an array transducer, and receives an ultrasound echo from the subject to create an ultrasound image, and a workstation connected to the ultrasound diagnostic device. The ultrasound diagnostic system comprises a storage unit that stores a plurality of ultrasound images in past diagnosis of a plurality of subjects as past images. The workstation has an input unit for allowing an operator to input various kinds of information, a workstation-side display unit, and a workstation-side control unit that controls display in the workstation-side display unit. In a case where a routine test in which a plurality of parts of the subject are sequentially subjected to ultrasound diagnosis in accordance with a determined procedure is performed and in a case where information on the subject is input from the input unit, the workstation-side control unit makes the workstation-side display unit perform a first display in which a plurality of past images in a past routine test of the subject stored in the storage unit are displayed as a thumbnail list and then perform a second display in which one past image and a current image including an ultrasound image newly created in the ultrasound diagnostic device with respect to a part corresponding to the one past image are displayed side by side on a past image region and a current image region adjacent to each other, in an arrangement order of the plurality of past images displayed as the thumbnail list in the first display.

Moreover, it is preferable that the workstation has a time setting unit that sets a transition time taken until the first display of the workstation-side display unit transitions to the second display, and the workstation-side control unit makes the display in the workstation-side display unit automatically transition from the first display to the second display after elapse of the transition time set in the time setting unit from a time point when the first display is performed.

Moreover, it is preferable that the time setting unit sets a set time input by the operator via the input unit as the transition time.

Alternatively the time setting unit may determine the transition time on the basis of a plurality of the transition times in a plurality of times of past ultrasound diagnosis.

Additionally, it is preferable that, in a case where information indicating that the transition time taken until the first display transitions to the second display is changed is input by the operator via the input unit, the workstation-side control unit shortens or extends a time taken for transition from a time point during the first display to the second display in the workstation-side display unit.

Additionally, it is preferable that, in a case where information indicating that the second display is made to transition to the first display is input by the operator via the input unit, the workstation-side control unit makes the second display in the workstation-side display unit transition to the first display.

Additionally, it is preferable that the workstation-side control unit makes the workstation-side display unit display a next past image in the arrangement order of the first display on the past image region in the second display after the second display of the current image corresponding to the one past image is performed and makes the current image region blank until a current image corresponding to the next past image is created by the ultrasound diagnostic device and displayed on the current image region from a time point when the next past image is displayed on the past image region.

Additionally, it is preferable that the workstation-side control unit makes the workstation-side display unit display past images displayed before and after the one past image in the arrangement order of the first display, side by side on both sides of the one past image displayed on the past image region in the second display, so as to be smaller than the one past image.

Moreover, it is preferable that the workstation-side control unit makes the workstation-side display unit display an ultrasound image created immediately before the current image in a current routine test, on one side of the current image displayed on the current image region in the second display in correspondence with the one past image, so as to be smaller than the current image.

Additionally, it is preferable that the workstation-side control unit makes the workstation-side display unit display the past image in the second display on the past image region so as to be larger than the current image displayed on the current image region.

Additionally, it is preferable that the workstation-side control unit makes the workstation-side display unit display the past image region and the current image region in the second display adjacent to each other left and right or up and down and display the past image and the current image side by side.

Additionally, it is preferable that the workstation-side control unit makes the workstation-side display unit display the plurality of past images as the thumbnail list on the past image region and display a plurality of current images created in a current routine test as a thumbnail list on the current image region after a last past image in the arrangement order of the first display and a current image corresponding to the last past image are displayed on the past image region and the current image region in the second display.

Additionally, it is preferable that the workstation-side control unit makes the workstation-side display unit display at least one or more selected images selected on the basis of information indicating that images input by the operator via the input unit are selected, as a thumbnail list at a rearmost end of the plurality of past images in the arrangement order of the first display, and display the one or more selected images subsequent to the plurality of past images on the past image region in the second display.

Additionally, the method of controlling an ultrasound diagnostic system is a method of controlling an ultrasound diagnostic system including an ultrasound diagnostic device that transmits an ultrasound beam toward a subject from an array transducer, and receives an ultrasound echo from the subject to create an ultrasound image, and a workstation connected to the ultrasound diagnostic device. The method comprises storing a plurality of ultrasound images in past diagnosis of a plurality of subjects as past images; and, in a case where a routine test in which a plurality of parts of the subject are sequentially subjected to ultrasound diagnosis in accordance with a determined procedure is performed and in a case where information on the subject is input, making a workstation-side display unit of the workstation perform a first display in which a plurality of past images in a past routine test of the subject that are stored are displayed as a thumbnail list and then perform a second display in which one past image and a current image including an ultrasound image newly created in the ultrasound diagnostic device with respect to a part corresponding to the one past image are displayed side by side on a past image region and a current image region adjacent to each other, in an arrangement order of the plurality of past images displayed as the thumbnail list in the first display.

According to the invention, the operator of the ultrasound diagnostic device can carry out the screening test while checking the list of the past diagnostic images of the subject displayed on the display unit of the workstation, and can efficiently perform the ultrasound diagnosis.

DESCRIPTION OF THE PREFERRED EMBODIMENTS

Hereinafter, embodiments of the invention will be described with reference to the accompanying drawings.

Embodiment 1

Figure 1:
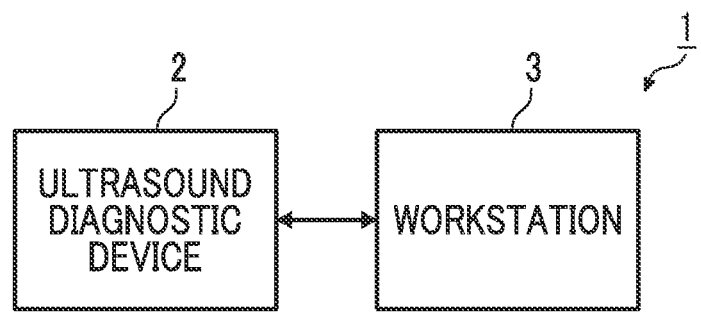
FIG. 1 is a block diagram illustrating an example of the configuration of an ultrasound diagnostic system of the embodiment of the invention.

The configuration of an ultrasound diagnostic system related to Embodiment 1 of the invention is illustrated in FIG. 1. An ultrasound diagnostic system 1 has an ultrasound diagnostic device 2 that creates an ultrasound image (hereinafter referred to as an ultrasound diagnosis image), and a workstation 3 connected to the ultrasound diagnostic device 2. The ultrasound diagnostic device 2 and the workstation 3 are connected to each other so as to communicate in both directions using connecting means, such as a cable local area network (LAN), a wireless LAN, and a universal serial bus (USB).

Figure 2:
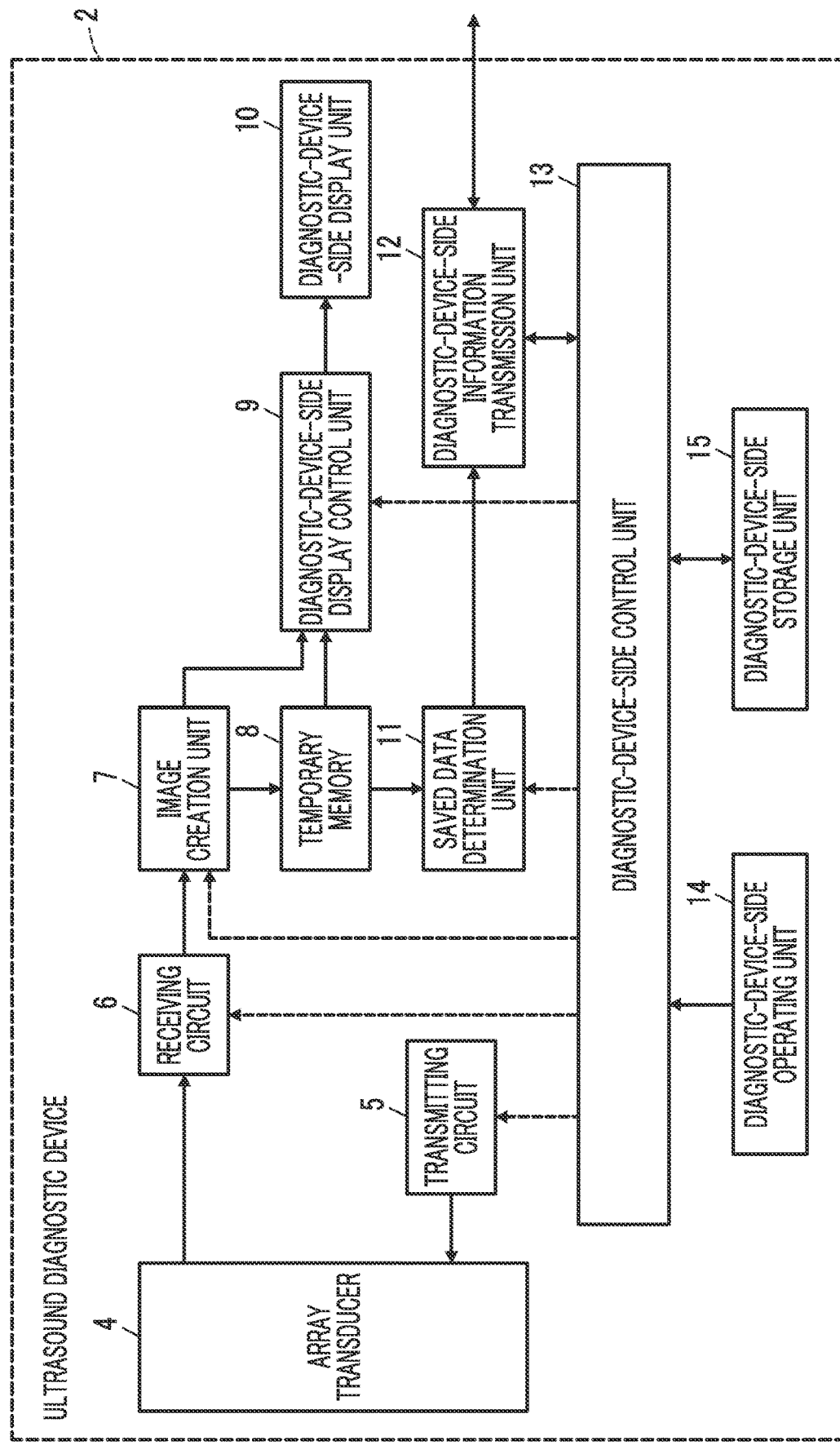
FIG. 2 is a block diagram illustrating an internal configuration of the ultrasound diagnostic device of FIG. 1 in Embodiment 1.

As illustrated in FIG. 2, the ultrasound diagnostic device 2 comprises an array transducer 4, and a transmitting circuit 5 and a receiving circuit 6 are connected to the array transducer 4. An image creation unit 7, a diagnostic-device-side display control unit 9, and a diagnostic-device-side display unit 10 are sequentially connected to the receiving circuit 6. Additionally, the image creation unit 7 has a temporary memory 8 connected thereto, and the temporary memory 8 is connected to the diagnostic-device-side display control unit 9. Moreover, a saved data determination unit 11 and a diagnostic-device-side information transmission unit 12 are sequentially connected to the temporary memory 8.

Moreover, a diagnostic-device-side control unit 13 is connected to the transmitting circuit 5, the receiving circuit 6, the image creation unit 7, the diagnostic-device-side display control unit 9, the saved data determination unit 11, and the diagnostic-device-side information transmission unit 12, and a diagnostic-device-side operating unit 14 and a diagnostic-device-side storage unit 15 are connected to the diagnostic-device-side control unit 13, respectively. In addition, the diagnostic-device-side information transmission unit 12 is connected to the diagnostic-device-side control unit 13 so as to be capable of transferring information in both directions.

Figure 3:
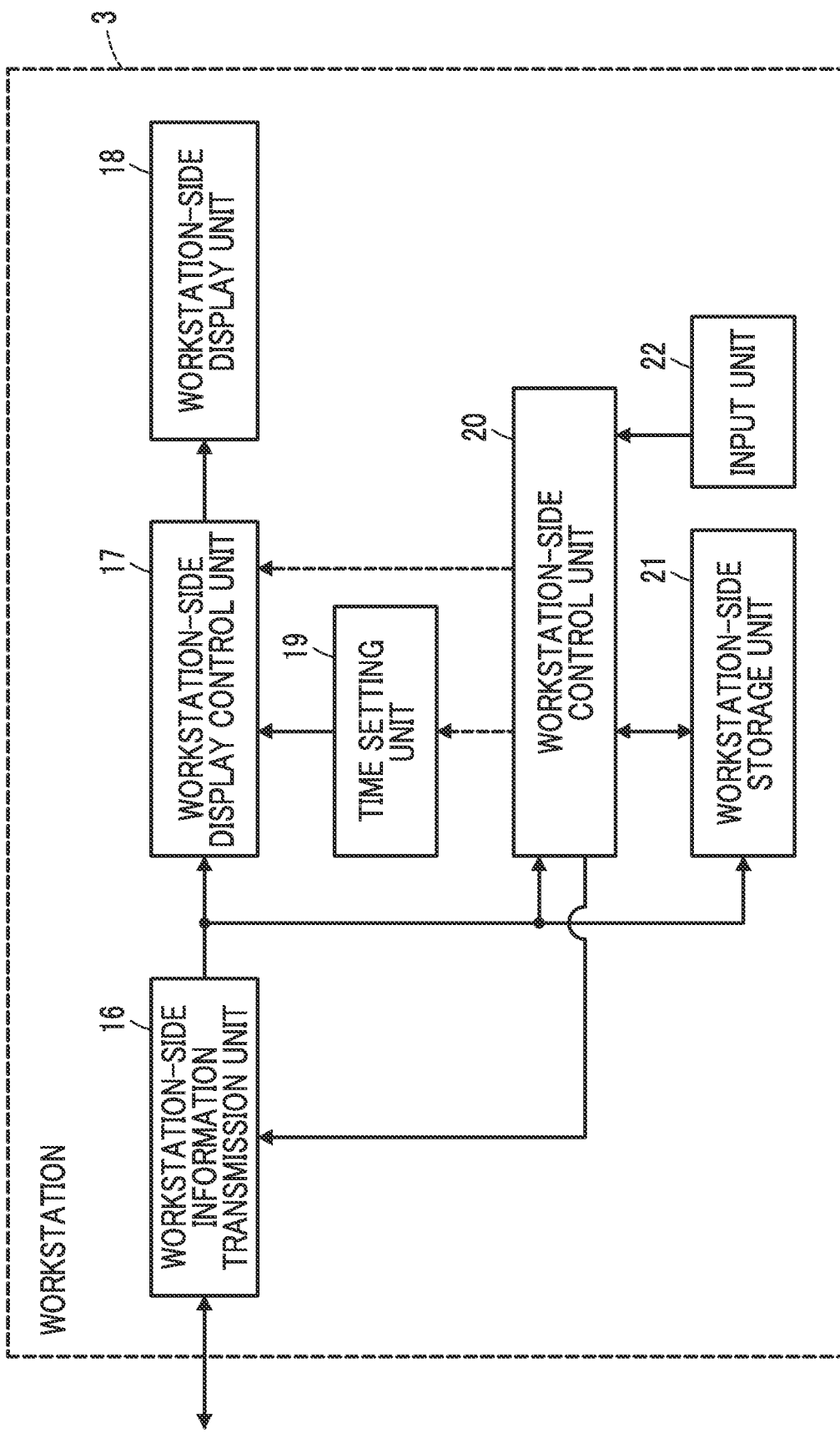
FIG. 3 is a block diagram illustrating an internal configuration of a workstation of FIG. 1 in Embodiment 1.

Additionally, as illustrated in FIG. 3, the workstation 3 has a workstation-side information transmission unit 16 capable of transmitting information in both directions with respect to the diagnostic-device-side information transmission unit 12 of the ultrasound diagnostic device 2. A workstation-side display control unit 17 and a workstation-side display unit 18 are sequentially connected to the workstation-side information transmission unit 16. Additionally, a time setting unit 19 is connected to the workstation-side display control unit 17. Moreover, a workstation-side control unit 20 is connected to the workstation-side information transmission unit 16, the workstation-side display control unit 17, and the time setting unit 19, and a workstation-side storage unit 21 and an input unit 22 are connected to the workstation-side control unit 20, respectively.

The array transducer 4 of the ultrasound diagnostic device 2 illustrated in FIG. 2 has a plurality of elements (ultrasound transducers) that are arranged in one dimension or two dimensions. These elements transmit ultrasound waves in accordance with driving signals supplied from the transmitting circuit 5, and receive ultrasound echoes from the subject to output the received signals. The respective elements are configured, for example, using oscillators in which electrodes are formed at both ends of piezoelectric bodies including piezoelectric ceramics represented by lead zirconate titanate (PZT), polymer piezoelectric elements represented by poly vinylidene di fluoride (PVDF), and piezoelectric single crystals represented by lead magnesium niobate-lead titanate (PMN-PT).

In a case where a pulse-like or continuous-wave-like voltage is applied to the electrodes of such oscillators, piezoelectric bodies expand and contract, pulse-like or continuous-wave ultrasound waves are generated from the respective oscillators, and an ultrasound beam is formed from a synthetic wave of those ultrasound waves. Additionally, the respective oscillators receive the propagating ultrasound waves, thereby expanding and contracting to generate electrical signals, and the electrical signals are output from the respective oscillators to the receiving circuit 6 as received signals of the ultrasound waves.

The transmitting circuit 5 includes, for example, a plurality of pulse generators, and adjusts the amounts of delay of the respective driving signals to supply the adjusted amounts of delay to the plurality of elements such that the ultrasound waves transmitted from the plurality of elements of the array transducer 4 form the ultrasound beam, on the basis of on a transmission delay pattern selected in accordance with a control signal from the diagnostic-device-side control unit 13.

Figure 4:
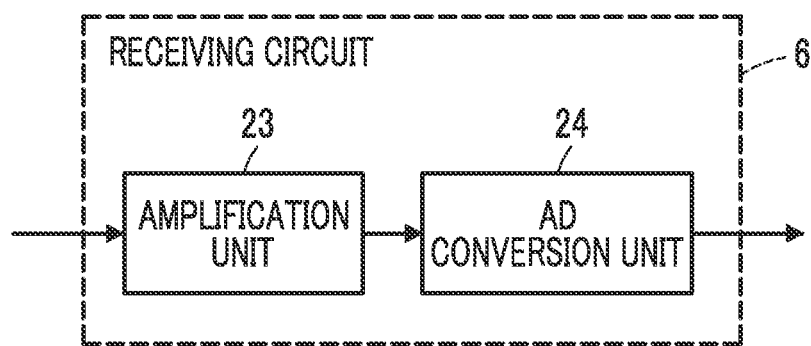
FIG. 4 is a block diagram illustrating an internal configuration of a receiving circuit of FIG. 2 in Embodiment 1.

As illustrated in FIG. 4, the receiving circuit 6 has a configuration in which an amplification unit 23 and an analog/digital (AD) conversion unit 24 are connected in series. The receiving circuit 6 amplifies the received signals output from the respective elements of the array transducer 4 in the amplification unit 23, and outputs the element data obtained by being digitized in the AD conversion unit 24 to the image creation unit 7.

Figure 5:
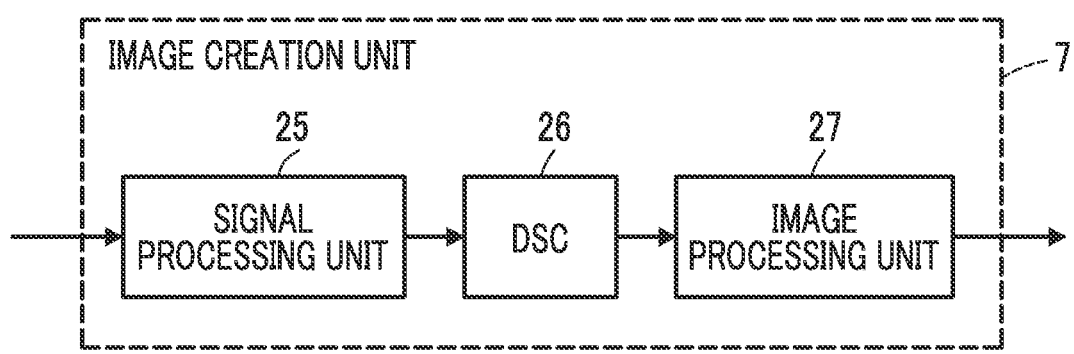
FIG. 5 is a block diagram illustrating an internal configuration of an image creation unit of FIG. 2 in Embodiment 1.

As illustrated in FIG. 5, the image creation unit 7 has a configuration in which a signal processing unit 25, a digital scan converter (DSC) 26, and an image processing unit 27 are sequentially connected in series.

The signal processing unit 25 performs reception focus processing in which addition (phasing addition) is performed by delaying respective element data items in accordance with a set sonic speed on the basis of a reception delay pattern selected in accordance with the control signal from the diagnostic-device-side control unit 13. Sound ray signals in which the ultrasound echoes are focused are created by this reception focus processing. Moreover, the signal processing unit 25 performs correction of damping, resulting from propagation distances in accordance with the depths of the reflection positions of the ultrasound waves, with respect to the sound ray signals, and performs envelope detection processing to create brightness-mode (B-mode) image signals that are tomographic image information on the tissue within the subject.

The DSC 26 converts the B-mode image signals created in the signal processing unit 25 into image signals according to a scanning mode of normal television signals (raster conversion).

The image processing unit 27 outputs the B-mode image signals to the diagnostic-device-side display control unit 9 after various kinds of required image processing, such as gradation processing, is performed on the B-mode image signals input from the DSC 26.

As illustrated in FIG. 2, the temporary memory 8 of the ultrasound diagnostic device 2 temporarily saves moving image data including a plurality of B-mode images continuously created in the image creation unit 7. The moving image data temporarily saved in the temporary memory 8 is data until a past given time determined from a current scanning time point, and is output to the diagnostic-device-side display control unit 9 or the saved data determination unit 11 as the moving image data or as still image data cut down from the moving image data.

As illustrated in FIG. 2, the diagnostic-device-side display control unit 9 of the ultrasound diagnostic device 2 makes the diagnostic-device-side display unit 10 display the moving image constituted of the ultrasound diagnosis image, or the ultrasound diagnosis image, on the basis of the B-mode image signals that are created in the image creation unit 7 and input via the temporary memory 8.

The diagnostic-device-side display unit 10 includes, for example, display units, such as a liquid crystal display (LCD), and displays the ultrasound diagnosis image under the control of the diagnostic-device-side display control unit 9.

The saved data determination unit 11 of the ultrasound diagnostic device 2 determines the moving image data or still image data (saved data) to be saved in the workstation-side storage unit 21 via the diagnostic-device-side information transmission unit 12 and the workstation-side information transmission unit 16 among the moving image data temporarily saved in the temporary memory 8 or the still image data cut down from the moving image data, and outputs the determined the moving image data or still image data to the diagnostic-device-side information transmission unit 12. In the example illustrated in FIGS. 2 and 3, in the saved data determination unit 11, the moving image data or still image data determined as the saved data is saved in the workstation-side storage unit 21 via the diagnostic-device-side information transmission unit 12 and the workstation-side information transmission unit 16, under the control of the diagnostic-device-side control unit 13 based on the information input by an operator (hereinafter simply referred to as an operator) of the ultrasound diagnostic system 1 using the diagnostic-device-side operating unit 14.

The diagnostic-device-side information transmission unit 12 of the ultrasound diagnostic device 2 transmits the moving image data or still image data output from the saved data determination unit 11 and various kinds of information output from the diagnostic-device-side control unit 13 to the workstation-side information transmission unit 16 of the workstation 3. The various kinds of information output from the diagnostic-device-side control unit 13 include, for example, information or the like for controlling the workstation 3. Moreover, the diagnostic-device-side information transmission unit 12 receives various kinds of information output from the workstation-side information transmission unit 16, and outputs the received information to the diagnostic-device-side control unit 13. The various kinds of information received from the workstation-side information transmission unit 16 include, for example, information on the subject, parameters of the ultrasound image, such as brightness and contrast set in the past in conformity with the subject. In this way, the diagnostic-device-side information transmission unit 12 not only transmits various kinds of information from the ultrasound diagnostic device 2 to the workstation 3 but also is used together with the workstation-side information transmission unit 16, thereby allowing bidirectional communication between the ultrasound diagnostic device 2 and the workstation 3.

The diagnostic-device-side control unit 13 controls the respective units of the ultrasound diagnostic device 2 on the basis of a command input via the diagnostic-device-side operating unit 14 by the operator.

The diagnostic-device-side operating unit 14 is for the operator to perform an input operation, and can be configured to comprise a keyboard, a mouse, a trackball, a touch panel, and the like.

The diagnostic-device-side storage unit 15 stores a plurality of ultrasound images in the past diagnosis of a plurality of subjects as past images and stores operating programs of the ultrasound diagnostic device 2, and a memory medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), or a server can be used as the diagnostic-device-side storage unit. In addition, although the image creation unit 7, the diagnostic-device-side display control unit 9, the saved data determination unit 11, the diagnostic-device-side information transmission unit 12, and the diagnostic-device-side control unit 13 are constituted of a central processing unit (CPU) and operating programs for making the CPU perform various kinds of processing, these may be configured using a digital circuit. Additionally, the image creation unit 7, the diagnostic-device-side display control unit 9, the saved data determination unit 11, the diagnostic-device-side information transmission unit 12, and the diagnostic-device-side control unit 13 can also be configured so as to be partially or entirely integrated into one CPU.

As illustrated in FIG. 3, the workstation-side information transmission unit 16 of the workstation 3 outputs the moving image data or still image data output from the diagnostic-device-side information transmission unit 12 of the ultrasound diagnostic device 2 to the workstation-side display control unit 17 and the workstation-side storage unit 21. Additionally, the workstation-side information transmission unit 16 outputs various kinds of information, which is input by the operator via the diagnostic-device-side operating unit 14 and output from the diagnostic-device-side information transmission unit 12, to the workstation-side control unit 20 and the workstation-side storage unit 21. Moreover, the workstation-side information transmission unit 16 transmits various kinds of information, such as the information on the subject output from the workstation-side control unit 20, to the diagnostic-device-side information transmission unit 12 of the ultrasound diagnostic device 2. All the above-mentioned output of the workstation-side information transmission unit 16 is controlled under the instruction of the workstation-side control unit 20.

The workstation-side display control unit 17 of the workstation 3 makes the workstation-side display unit 18 display the moving image or ultrasound diagnosis image constituted of the ultrasound diagnosis image, on the basis of the B-mode image signals of the saved data received and output from the diagnostic-device-side information transmission unit 12 of the ultrasound diagnostic device 2 by the workstation-side information transmission unit 16.

The workstation-side display unit 18 includes, for example, display devices, such as an LCD, and displays the ultrasound diagnosis image under the control of the workstation-side display control unit 17.

The time setting unit 19 of the workstation 3 sets display time about the display in the workstation-side display unit 18 on the basis of the instruction from the workstation-side control unit 20. The time setting unit 19 can set a value input by the operator via the input unit 22 as a set value of the display time. The operation of the time setting unit 19 will be described in detail below.

The workstation-side control unit 20 of the workstation 3 controls the respective units of the workstation 3 on the basis of the information stored in the workstation-side storage unit 21 and a command input by the operator via the input unit 22. The workstation-side storage unit 21 stores operating programs of the workstation 3, information on a plurality of subjects, medical images, such as a plurality of ultrasound images, endoscopic images, and radiological images, in the past diagnosis of the plurality of subjects, and the like.

As the workstation-side storage unit 21, for example, memory media, such as a hard disc, a flexible disc, an MO disc, an MT, a RAM, a CD, a DVD, SD card, and a USB memory, or storage units (not illustrated), such as a server outside the workstation 3, can be used similarly to the diagnostic-device-side storage unit 15.

The input unit 22 is for the operator to perform an input operation, and can be configured using a keyboard, a mouse, a trackball, a touch panel, and the like. Additionally, the input unit 22 may be configured using external user interfaces, such as a foot switch, which is a foot-operated switch connected from the outside, with respect to the workstation 3.

In addition, although the workstation-side information transmission unit 16, the workstation-side display control unit 17, the time setting unit 19, and the workstation-side control unit 20 are constituted of a CPU and operating programs for making the CPU perform various kinds of processing, these may be configured using a digital circuit. Additionally, the workstation-side information transmission unit 16, the workstation-side display control unit 17, the time setting unit 19, and the workstation-side control unit 20 can also be configured so as to be partially or entirely integrated into one CPU.

Here, a display method performed in the workstation-side display unit 18 of the workstation 3 of the ultrasound diagnostic system 1 of the embodiment of the invention will be described with reference to FIGS. 6 and 7.

Figure 6:
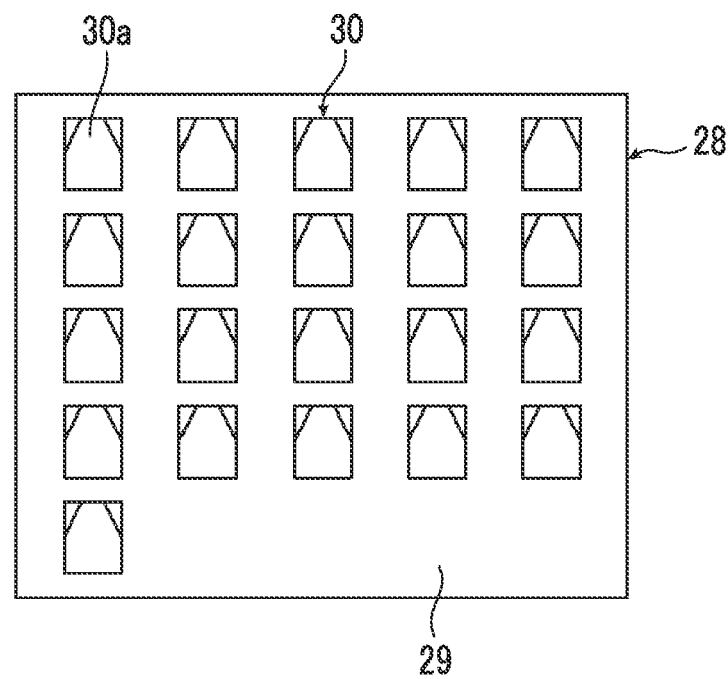
FIG. 6 is a conceptual diagram of an example illustrating a first display screen.

First, a first display screen 28 illustrated in FIG. 6 is displayed prior to a screening test in which a plurality of diagnosis parts of the subject are simply observed. The first display screen 28 has a thumbnail image display region 29 for displaying a plurality of thumbnail images, and a past image group 30 constituted of a plurality of past images displayed as thumbnails, such as past images 30a that are the ultrasound images of the subject diagnosed in the past, is displayed on the thumbnail image display region 29. In this way, thumbnail list display of the past image group 30 performed in the first display screen 28 is referred to as a first display.

Figure 7:
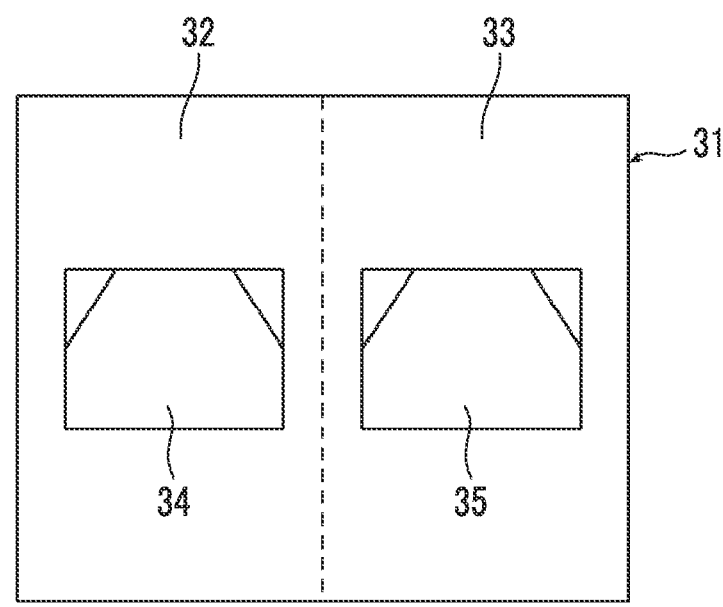
FIG. 7 is a conceptual diagram of an example illustrating a second display screen.

In a case where the plurality of diagnosis parts are sequentially diagnosed after the screening test, a second display screen 31 as illustrated in FIG. 7 is displayed. The second display screen 31 has a past image region 32 and a current image region 33 that are two regions adjacent to each other. In the second display screen 31, one past image 34, and a current image 35 constituted of an ultrasound image newly created in the ultrasound diagnostic device 2 with respect to a part corresponding to the one past image 34 are displayed side by side on the past image region 32 and the current image region 33 adjacent to each other. In this way, displaying the past image region 32 and the current image region 33 adjacent to each other, which is performed in the second display screen 31, is referred to as a second display.

Next, the operation of the ultrasound diagnostic system 1 will be described, referring to display screens in the workstation-side display unit 18 illustrated in FIGS. 8 to 11.

Figure 8:
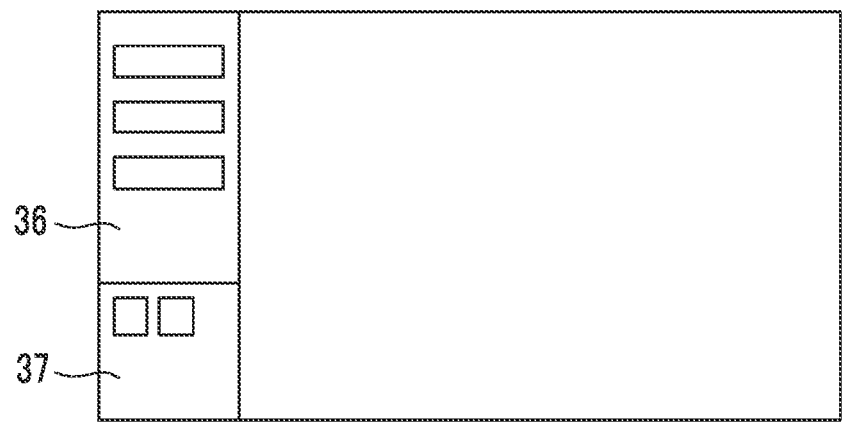
FIG. 8 is a conceptual diagram of an example illustrating a screen to which various kinds of information are input.

In a case where a routine test in which the plurality of parts of the subject are sequentially and ultrasonically diagnosed in accordance with a determined procedure is started, first, the operator inputs the information on the subject, which is a target subjected to current ultrasound diagnosis in a display screen in the workstation-side display unit 18 illustrated in FIG. 8, via the input unit 22 of the workstation 3. As illustrated in FIG. 8, the display screen of the workstation-side display unit 18 has an information display input region 36, a list display selection region 37, and a blank region. The operator inputs the information on the subject to a plurality of text boxes displayed on the information display input region 36. The information on the subject input to the plurality of text boxes includes identification data or an identifier (ID), a name, an age, a sex, and the like of the subject. Here, the ID of the subject is an identifier for managing the past diagnosis of each subject. In a case where the operator inputs the information on the subject, for example, in a case where the operator inputs the ID of the subject to a text box of the information display input region 36, the information on the subject stored in the workstation-side storage unit 21 may be read, and information other than the ID of the subject may be automatically input to the plurality of remaining text boxes under the control of the workstation-side control unit 20 and the workstation-side display control unit 17.

Additionally, the operator inputs the set value of the time set in the time setting unit 19 of the workstation 3 while the display screen illustrated in FIG. 8 is displayed in the workstation-side display unit 18. The set value of the time set in the time setting unit 19 includes a transition time that is taken from a time point when the first display illustrated in FIG. 6 is displayed to the transition to the second display illustrated in FIG. 7, in the workstation-side display unit 18. Additionally, as input means for inputting the set value of the time set in the time setting unit 19, for example, a text box provided in the information display input region 36 or the list display selection region 37 may be used. Additionally, for example, the set value of the time may be input in a window that is popup-displayed by selecting selected a button provided in the information display input region 36 or the list display selection region 37.

In a case where the operator inputs the information on the subject to a text box displayed on the information display input region 36, a list of past routine tests of the subject stored in the workstation-side storage unit 21 is displayed in the list display selection region 37. As the list of the past routine tests, for example, typical images acquired in the respective routine tests are displayed as a thumbnail list, and texts indicating titles input in advance with respect to respective diagnosis items are displayed as a list. The operator selects and determines one routine test using determination means, such as a determination button displayed on the list display selection region 37 or the input unit 22 of the workstation 3, among the plurality of past routine tests of the subject displayed on the list as described above. For example, the ultrasound diagnosis executed in the latest past is selected and determined from the plurality of past diagnosis items.

Figure 9:
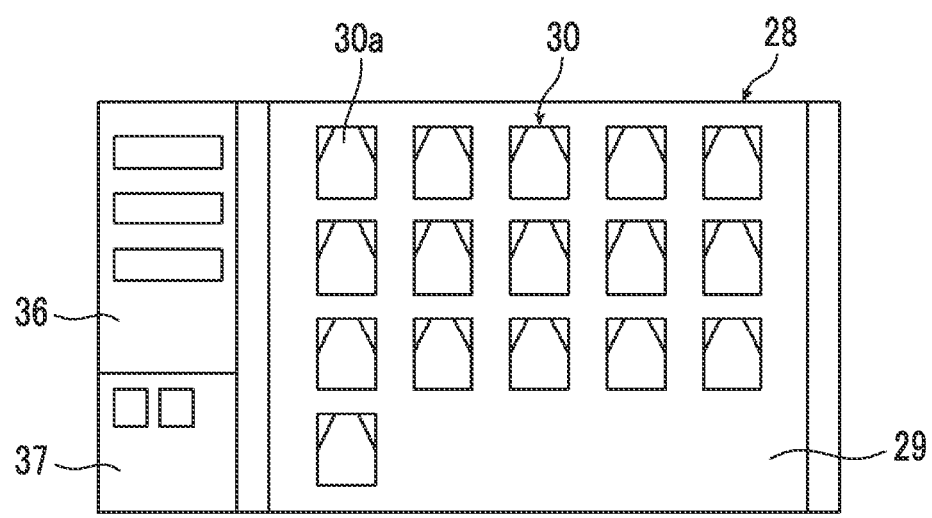
FIG. 9 is a conceptual diagram of an example illustrating a screen including first display of a past image of a subject.

In a case where one of the past routine tests displayed as the list on the list display selection region 37 is selected and determined by the operator, as illustrated in FIG. 9, the first display of the plurality of past images of the routine test selected and selected by the operator is performed in the blank region of FIG. 8. The past image group 30 in the past routine tests is stored in the workstation-side storage unit 21, and the first display is performed in the workstation-side display unit 18 under the control of the workstation-side display control unit 17.

Additionally, in a case where the routine test executed in the past by the operator is selected and determined, the workstation-side control unit 20 of the workstation 3 controls the workstation-side information transmission unit 16 so as to transmit the information on the subject stored in the workstation-side storage unit 21, and various conditions in a case where the ultrasound diagnosis is performed using the ultrasound diagnostic device 2. Imaging conditions of the ultrasound image in the ultrasound diagnostic device 2 and image creation conditions in a case where the element data is converted into the ultrasound image, and the like are included in the various conditions in a case where the ultrasound diagnosis is performed using the ultrasound diagnostic device 2. The diagnostic-device-side control unit 13 controls the ultrasound diagnostic device 2 on the basis of information and test conditions of the subject that are transmitted from the workstation-side information transmission unit 16 and received in the diagnostic-device-side information transmission unit 12 of the ultrasound diagnostic device 2. In this way, in a case where the ultrasound diagnostic device 2 and the workstation 3 are connected to each other so that information can be transmitted in both directions, the information on the subject input in the workstation-side display unit 18 and the various conditions in a case where the ultrasound diagnosis is performed using the ultrasound diagnostic device 2 are automatically set at the ultrasound diagnostic device 2 together with the first display of the plurality of past images in the workstation-side display unit 18, that is, the past image group 30. In addition, for example, in a case where the ultrasound diagnostic device 2 and the workstation 3 are not connected to each other so that information can be transmitted in both directions, such as in a case where only transmission of information from the ultrasound diagnostic device 2 to a workstation 3 is possible, setting on the ultrasound diagnostic device 2 can be performed using input means, such as a manual input.

As illustrated in FIG. 9, while the first display of the past image group 30 is performed in the workstation-side display unit 18, the operator can perform the screening test in which a diagnosis part in the current routine test is checked using the ultrasound diagnostic device 2, referring to the first display. That is, in this case, a live moving image corresponding to the element data currently received from the array transducer 4 of the ultrasound diagnostic device 2 can be displayed on the diagnostic-device-side display unit 10, and the operator can compare this live moving image with the first display. Additionally, in the screening test, since the ultrasound image is not saved, ultrasound image data created in the image creation unit 7 of the ultrasound diagnostic device 2 is output to the diagnostic-device-side display control unit 9 without using the temporary memory 8. In this way, in the ultrasound diagnostic system 1 of the embodiment of the invention, the operator can perform the screening test, while comparing the past image group 30 in the past routine tests displayed on the workstation-side display unit 18 with the live moving image that is the current ultrasound image displayed the diagnostic-device-side display unit 10.

Figure 10:
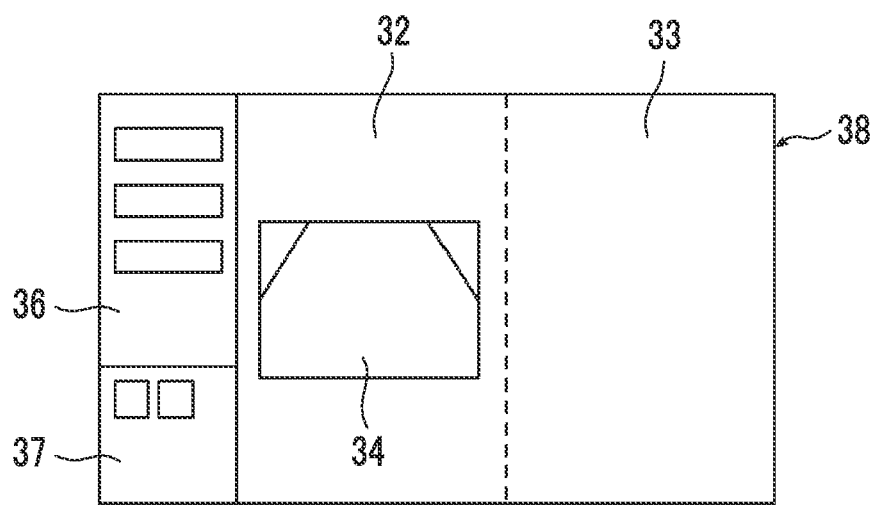
FIG. 10 is a conceptual diagram of an example illustrating a screen on which only the past image is displayed, in second display.

The first display of the past image group 30 illustrated in FIG. 9 automatically transitions to the second display after the elapse of the time set in the time setting unit 19. FIG. 10 illustrates a second display screen 38 that transitions to the next of the first display screen 28 illustrated in FIG. 9, in the workstation-side display unit 18. While the second display screen 38 illustrated in FIG. 10 is displayed on the workstation-side display unit 18, the workstation-side information transmission unit 16 does not receive B-mode image data corresponding to the past image 34. In that case, the current image region 33 of the second display screen 38 becomes blank, as illustrated in FIG. 10. In addition, an image displayed as the past image 34 is one among the plurality of past images that constitute the past image group 30 in the first display. Additionally, as will be described below, the past image 34 is sequentially displayed on the past image region 32 in arrangement order of the past image group 30 in the first display, that is, in time-series order of the ultrasound images created the past routine tests. Hereinafter, in the example in FIG. 8, the past image group 30 will be described supposing that the alignment order from the left to the right and from the upper stage to the lower stage in the figure is the arrangement order of the past image group 30.

In addition, the transition time until the first display of the past image group 30 illustrated in FIG. 9 automatically transitions to the second display illustrated in FIG. 10 is set by the time setting unit 19 of the workstation 3 on the basis of a set time input by the operator via the input unit 22 of the workstation 3. Additionally, this transition time may be set by the time setting unit 19 on the basis of a predetermined set value stored in the workstation-side storage unit 21. In addition, the set time input by the operator via the input unit 22 may be stored in the workstation-side storage unit 21 in association with information, such as the ID of the subject, and the set transition time may be used for each diagnosis.

As illustrated in FIG. 10, while the second display screen 38 is displayed in the workstation-side display unit 18, the operator performs ultrasound diagnosis of the part of the subject corresponding to the one past image 34 displayed on the past image region 32 using the ultrasound diagnostic device 2. In this case, the operator searches for a part where an ultrasound image is created, while comparing the live moving image displayed on the diagnostic-device-side display unit 10 with the past image 34. In a case where the ultrasound image is created using the ultrasound diagnostic device 2, the operator stops (freezes) the live moving image displayed on the diagnostic-device-side display unit 10, in a scanning location corresponding to the past image 34, and makes the saved data determination unit 11 determine an ultrasound image to be saved, via the diagnostic-device-side operating unit 14 and the diagnostic-device-side control unit 13 of the ultrasound diagnostic device 2. In this case, a moving image that is saved in the temporary memory 8 of the ultrasound diagnostic device 2 and that is constituted of ultrasound images from a time point where the live moving image is stopped to a predetermined past time, can be displayed on the diagnostic-device-side display unit 10. For example, a keyboard, a trackball, a foot switch, and the like that constitute the diagnostic-device-side operating unit 14 may be used as means for selecting and determining one of the plurality of ultrasound images that constitute the moving image. That is, for example, although selection and determination means, such as operating the trackball to select a desired time of the moving image and determining an ultrasound image of the selected time using a key of the keyboard, can be used, it is needless to say that the invention is not limited to the above as long as any means using the diagnostic-device-side operating unit 14 is adopted. In a case where one ultrasound image is determined as the saved data, a B-mode image corresponding to this one ultrasound image is transmitted to the workstation-side information transmission unit 16 via the diagnostic-device-side information transmission unit 12. In addition, in a case where the one ultrasound image is determined as the saved data, the moving image data referred to by freezing the display of the diagnostic-device-side display unit 10 may be transmitted to the workstation-side information transmission unit 16 via the diagnostic-device-side information transmission unit 12 and may be stored in the workstation-side storage unit 21.

Figure 11:
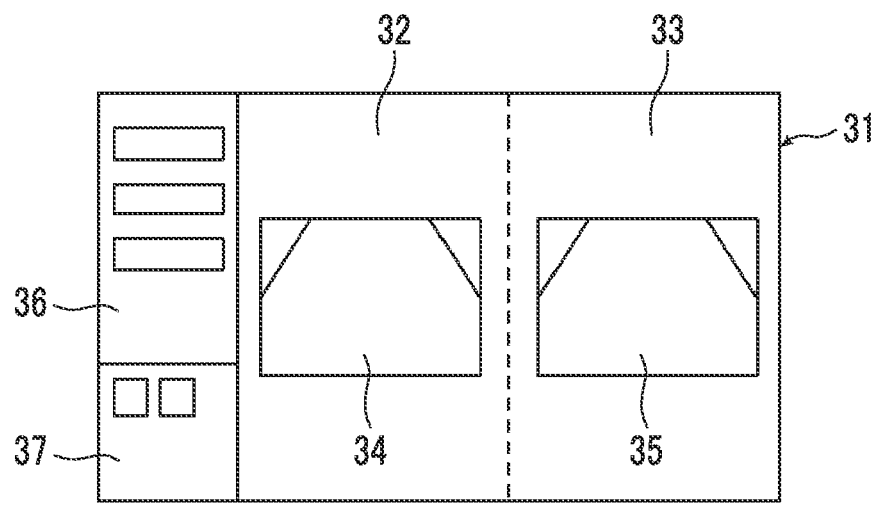
FIG. 11 is a conceptual diagram of an example illustrating a screen on which the past image and a current image of the subject are displayed, in the second display.

In a case where B-mode image data corresponding to the one ultrasound image is received by the workstation-side information transmission unit 16, as illustrated in FIG. 11, the B-mode image data is displayed on the current image region 33 in the workstation-side display unit 18 as the current image 35 corresponding to the past image 34 via the workstation-side display control unit 17. The current image 35 is constituted of the ultrasound image newly created in the ultrasound diagnostic device 2 to the part corresponding to the past image 34. In this way, the second display screen 31 in which the past image 34 and the current image 35 are respectively displayed side by side on the past image region 32 and the current image region 33 is displayed in the workstation-side display unit 18.

In a case where information indicating that the freezing of the display of the diagnostic-device-side display unit 10 is cancelled is output to the diagnostic-device-side display control unit 9 via the diagnostic-device-side operating unit 14 and the diagnostic-device-side control unit 13 of the ultrasound diagnostic device 2 after the second display of the past image 34 and the current image 35 corresponding thereto is performed, the display of the diagnostic-device-side display unit 10 transitions to the live moving image. The information indicating that the freezing of the display of this diagnostic-device-side display unit 10 is cancelled is output to the workstation-side information transmission unit 16 via the diagnostic-device-side control unit 13 and the diagnostic-device-side information transmission unit 12 and further output to the workstation-side control unit 20. In this case, the workstation-side control unit 20 controls the workstation-side display control unit 17 such that the display in the workstation-side display unit 18 is made to transition from the second display in which the past image 34 and the current image 35 are displayed to the second display in which the next past image is displayed. Here, the next past image means a past image located one position after the past image 34 in the arrangement order of the first display of the past image group 30. In this way, the past images are sequentially displayed in the arrangement order of the first display of the past image group 30 on the past image region 32 in the second display. Additionally, a blank and the current image 35 corresponding to each past image 34 are alternately and sequentially displayed on the current image region 33 in the second display. The transition from the second display in the workstation-side display unit 18 to the second display corresponding to the next past image is repeatedly performed until all the routine tests corresponding to the past image group 30 in the first display are completed.

As described above, according to the ultrasound diagnostic system 1 of the embodiment of the invention, the first display of the past image group 30 in the workstation-side display unit 18 can be made to automatically transition to the second display after the elapse of the set transition time. For that reason, the operator can perform the screening test, referring to the past image group 30 and the current ultrasound image, using the workstation-side display unit 18 and the diagnostic-device-side display unit 10 that are different display units. Additionally, in a case where the operator ends the screening test, the operator does not need to perform the operation of the ultrasound diagnostic device 2 and the workstation 3 and can omit the operation for making the first display screen 28 displayed on the workstation-side display unit 18 transition to the second display screen 31 and easily transition to a routine test. Moreover, the operator can easily compare the past image 34 with the current image 35, using the workstation-side display unit 18 different from the diagnostic-device-side display unit 10. Additionally, the operator can perform the ultrasound diagnosis while checking that the current image 35 corresponding to the past image 34 has been saved in the workstation-side storage unit 21. Therefore, in the routine test, it is easy to check that the acquisition of the ultrasound image has failed.

Meanwhile, in Embodiment 1, the first display of the workstation-side display unit 18 automatically transitions to the second display after the elapse of the transition time set by the operator via the input unit 22 of the workstation 3. However, a configuration in which the transition time can be changed during the first display may be adopted. For example, in a case where the information indicating that the transition time is changed by the operator via the input unit 22 of the workstation 3 is input during the first display, the time taken to transition from a time point during the first display in the workstation-side display unit 18 to the second display is shortened or extended. In addition, the information indicating that the transition time is changed may be allocated to respective specific user interfaces, such as a key of the keyboard, the trackball, and the foot switch that constitute the input unit 22. In this case, for example, a specific key of the keyboard may be allocated for the shortening of the transition time, the foot switch may be allocated to the extension of the transition time, and the like.

Additionally, although a case where the information indicating that the transition time is set and changed is input by the operator via the input unit of the workstation 3 has been described above, the information indicating that the transition time is set and changed may be input via the diagnostic-device-side operating unit 14 of the ultrasound diagnostic device 2.

Additionally, in a case where the information indicating that the transition time is set and changed is input by the operator via the diagnostic-device-side operating unit 14, a transition time input screen for setting and changing the transition time can be displayed in the diagnostic-device-side display unit 10, though not illustrated. This transition time input screen may be displayed on the diagnostic-device-side display unit 10, for example, by operating the user interfaces, such as the keyboard that constitutes the diagnostic-device-side operating unit 14.

In that case, the information, indicating that the transition time is set and changed, which is input by the operator via the diagnostic-device-side operating unit 14, may be transmitted to the workstation-side information transmission unit 16 via the diagnostic-device-side control unit 13 and the diagnostic-device-side information transmission unit 12 and further input to the time setting unit 19 via the workstation-side control unit 20.

Additionally, although not illustrated, the ultrasound diagnostic device 2 may comprise the time setting unit. In that case, the information, indicating that the transition time is set and changed, which is input by the operator via the diagnostic-device-side operating unit 14 is input to the time setting unit of the ultrasound diagnostic device 2 via the diagnostic-device-side control unit 13. Moreover, the information on the transition time input to the time setting unit of the ultrasound diagnostic device 2 may be transmitted to the workstation-side information transmission unit 16 via the diagnostic-device-side information transmission unit 12 and further input to the workstation-side display control unit 17.

In addition, even in a case where the information indicating that the transition time is set and changed is input by the operator via the diagnostic-device-side operating unit 14, the information indicating that the transition time is set and changed may be allocated to respective specific user interfaces, such as a key of the keyboard, the trackball, and the foot switch that constitute the diagnostic-device-side operating unit 14.

Additionally, this transition time may be set by the time setting unit on the basis of the set value stored in the workstation-side storage unit 21. Moreover, the transition time can also be automatically set using a learning function, in the time setting unit 19. In this case, the transition time is automatically set on the basis of, for example, the transition time set on the basis of the set time input by the operator via the input unit 22 or the set time stored in the workstation-side storage unit 21, and the transition time that has actually elapsed as a result by that the time for transition from the time point during the first display to the second display is shortened or extended. That is, the time setting unit 19 may set an arithmetical average value, etc. of a plurality of actual transition times in past multiple ultrasound diagnoses as the transition time, or may use statistical methods, such as interval estimation, in calculation of the transition time. In addition, the learned transition time may be stored in the workstation-side storage unit 21 in association with the information, such as the ID of the subject, and the set transition time may be used for each diagnosis.

Additionally, in the workstation-side display unit 18, the diagnostic-device-side control unit 13 can make the second display transition to the first display again after the transition time set from the time point when the first display of the past image group 30 is performed elapses and the first display transitions to the second display. In this case, in the workstation-side display unit 18, the first display automatically transitions to the second display again after the elapse of the transition time set from the time point when the second display has transitioned to the first display. Of course, even in this case, the time taken to transition from the time point during the first display to the second display can be shortened or extended on the basis of the information input by the operator via the input unit 22 of the workstation 3.

According to the above-described configuration, the set transition time can be easily shortened or extended, and the first display of the past image group 30 can be displayed on the workstation-side display unit 18 at an operator's desired timing. For that reason, according to operator's skills, methods of the screening test, and the like, the transition between the first display and the second display in the workstation-side display unit 18 can be freely performed.

Additionally, a trigger for transitioning from the second display in which the past image 34 and the current image 35 are displayed to the second display in which the next past image is displayed is not limited to the cancellation of the freezing of the display of the diagnostic-device-side display unit 10. For example, after the freezing state of the display of the diagnostic-device-side display unit 10 is cancelled, the current image 35 being displayed on the current image region 33 of the second display screen 31 may be used as a trigger for transitioning to the second display in which the next past image is displayed. Additionally, for example, after the freezing state of the display of the diagnostic-device-side display unit 10 is cancelled, the time set for the time setting unit 19 having elapsed may be used as a trigger for transitioning to the second display in which the next past image is displayed. The time for transitioning from the second display to the next second display may be set for the time setting unit 19, for example, by being input in a display screen of the workstation-side display unit 18 illustrated in FIG. 8.

Additionally, in the transition between the second display of the past image 34 and the current image 35 and the second display in which the next past image is displayed, the workstation-side display control unit 17 may be made to control the workstation-side display unit 18 such that only a past image specified by the operator via the input unit 22 of the workstation 3 is displayed as the past image 34 displayed on the past image region 32. In this way, for example, in a case where a past image of an overlapping part is included in the past image group 30, a current image of the same part of the subject can be prevented from being duplicately created. Additionally, under an instruction from the operator via the diagnostic-device-side operating unit 14, in the workstation-side display unit 18, the second display in which only the past image 34 displayed in the last second display is displayed may be performed again after the second display is made to transition to the second display in which the next past image is displayed. By performing such transition of the display screens, for example, the operator can perform imaging of the ultrasound image of the same part, which is imaged immediately before, again in a case where the ultrasound image created in the ultrasound diagnostic device 2 is unsuitable for diagnosis.

Moreover, in the workstation-side display unit 18, the second display may be temporarily made to transition to the first display of the past image group 30. In this case, for example, during the second display in the workstation-side display unit 18, the operator may push a specific key of the keyboard or the like that constitutes the diagnostic-device-side operating unit 14 of the ultrasound diagnostic device 2 or the input unit 22 of the workstation 3, and may control the workstation-side display control unit 17 such that the second display performed in the workstation-side display unit 18 is made to transition to the first display. According to the above configuration, the operator can easily check a procedure or the like of the entire routine test during the routine test in which a current image corresponding to each past image is sequentially acquired.

Additionally, an ultrasound image can be captured even after the current images corresponding to the past image group 30 in which the first display as illustrated in FIGS. 6 and 9 is performed are altogether captured using the ultrasound diagnostic device 2. In that case, in the second display as illustrated in FIGS. 7, 10, and 11, the past images corresponding to the ultrasound images newly captured at the present time are insufficient. For that reason, although not illustrated, for example, a plurality of newly captured current images may be sequentially displayed on the current image region 33 with a past image at the rearmost end in the arrangement order of the past image group 30 in the first display being displayed on the past image region 32. Additionally, the past image region 32 may be made to be blank, and the plurality of newly captured current images may be sequentially displayed on the current image region 33. Additionally, in a case where a current image newly created in the ultrasound diagnostic device 2 is stored in the workstation-side storage unit 21 and in a case where a moving image including the current image as a still image is stored in the workstation-side storage unit 21, a plurality of the moving images corresponding to a plurality of the current images in the past image region 32 may be sequentially reproduced in a loop in time series.

Embodiment 2

In the second display of Embodiment 1 illustrated in FIG. 11, the one past image 34 and the current image 35 corresponding to the past image 34 are displayed side by side on the past image region 32 and the current image region 33 adjacent to each other. The arrangement of the past image region 32 and the current image region 33 is not particularly limited as long as these regions are located adjacent to each other. That is, as in Embodiment 1 illustrated in FIG. 11, the past image region 32 and the current image region 33 of the second display screen 31 may be adjacent to each other left and right, and as in Embodiment 2 illustrated in FIG. 12, a past image region 40 and a current image region 41 of a second display screen 39 may be adjacent to each other up and down.

Figure 12:
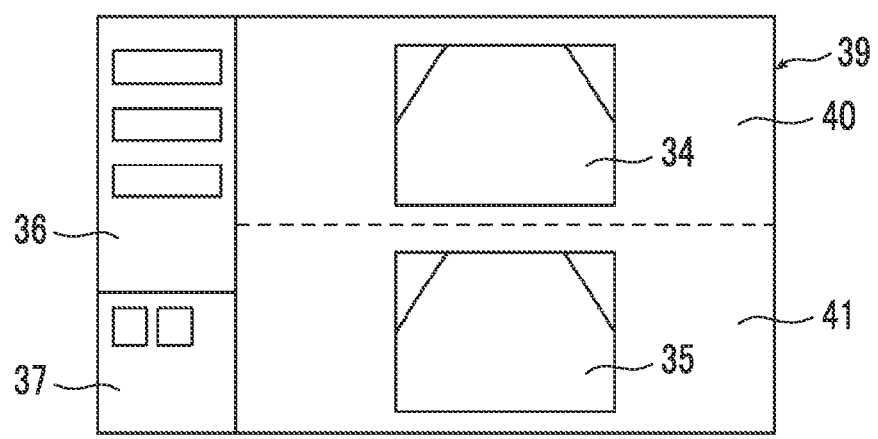
FIG. 12 is a conceptual diagram of an example illustrating a screen including the second display in Embodiment 2.

In addition, the configuration of the present Embodiment 2 is the same as that of the configuration of Embodiment 1 illustrated in FIGS. 1 to 11 except for the second display screen 39, the past image region 40, and the current image region 41 that are illustrated in FIG. 12. In FIG. 12, the same constituent elements as those of FIG. 11 will be designated by the same reference signs, and the detailed description of the constituent elements will be omitted.

Embodiment 3

Figure 13:
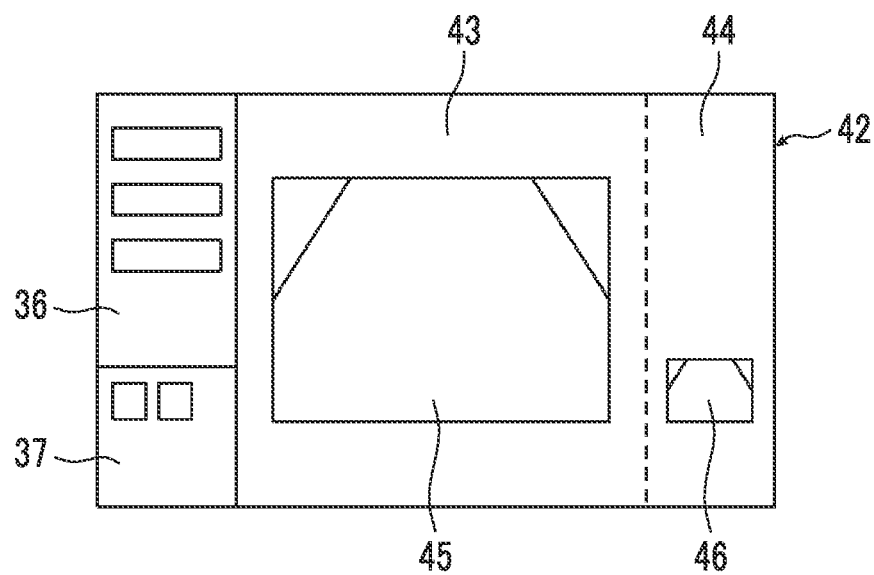
FIG. 13 is a conceptual diagram of an example illustrating a screen including the second display in Embodiment 3.
Figure 14:
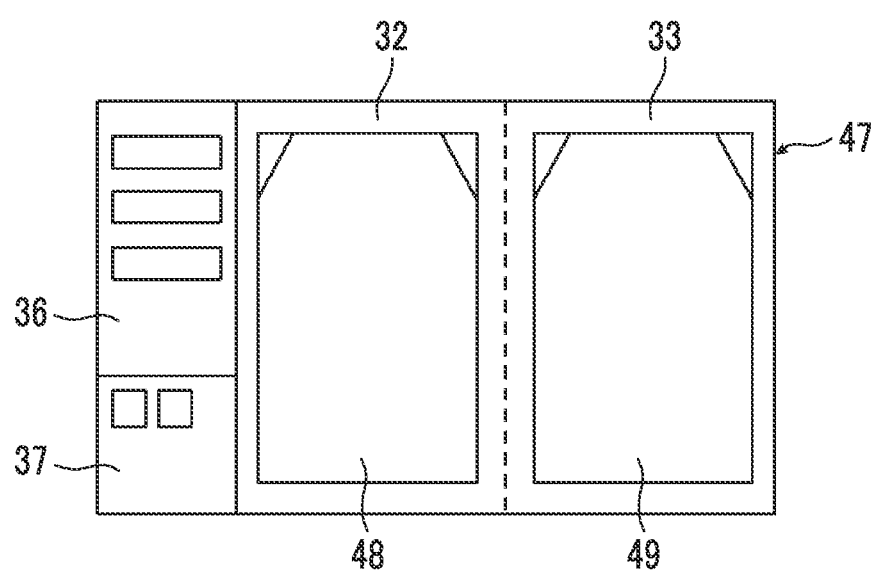
FIG. 14 is a conceptual diagram of another example illustrating the screen including the second display in Embodiment 3.

Additionally, in the second display of Embodiment 1 illustrated in FIG. 11, the past image region 32, the current image region 33, the past image 34, and the current image 35 may be displayed in an enlarged manner or displayed in a reduced manner, respectively. Hereinafter, Embodiment 3 illustrated in FIG. 13 is the same as the embodiment illustrated in FIGS. 1 to 11 except for a second display screen 42, a past image region 43, a current image region 44, a past image 45, and a current image 46, and a modification example of Embodiment 3 illustrated in FIG. 14 is the same as the embodiment illustrated in FIGS. 1 to 11 except for a second display screen 47, a past image 48, and a current image 49. For that reason, in FIGS. 13 and 14, the same constituent elements as FIG. 11 will be designated by the same reference signs, and the detailed description of the constituent elements will be omitted.

As illustrated in FIG. 13, the second display screen 42 displayed in the workstation-side display unit (not illustrated) has the past image region 43 of which the region area is enlarged, and the current image region 44 of which the region is reduced together with the enlargement of the past image region 43. Additionally, the past image 45 is displayed in an enlarged manner in the past image region 43, and the current image 46 is displayed in a reduced manner in the current image region 44. For that reason, for example, although not illustrated, even in a case where the operator performs the ultrasound diagnosis in a location slightly apart from a workstation disposed in the same clinic as the ultrasound diagnostic device, the ultrasound diagnosis can be performed while checking the past image 45 in detail.

Additionally, as illustrated in FIG. 13, the past image region 43 and the current image region 44 may not be enlarged or reduced, and only the past image and the current image may be enlarged or reduced. The second display screen 47 illustrated in FIG. 14 has the past image region 32 and the current image region 33 that have the same size as each other. The past image 48 and the current image 49 that are displayed in an enlarged manner are displayed side by side on the past image region 32 and the current image region 33. As a method of enlarging the past image 48 and the current image 49, although not illustrated, for example, the workstation-side display control unit may be controlled such that the past and current images 48 and 49 are enlarged by scaling factor set values from the centers of the past image 48 and the current image 49 on the basis of the scaling factor set values input by the operator via the input unit of the workstation and are displayed on the past image region 32 and the current image region 33. In this case, for example, the operator inputs the set values in the information display input region 36 or the list display selection region 37. In addition, the set values may be input prior to the routine test or may be input in a case where the workstation-side display unit performs the second display. Additionally, in a case where enlarged images exceed crosses the respective image regions with the enlargement of the past image 48 and the current image 49, only center portions in the enlarged images may be displayed, respectively.

Embodiment 4

In the second display screens 31, 38, 39, 42, and 47 of Embodiments 1 to 3 illustrated in FIGS. 7 and 11 to 14, one past image 34, 45, or 48 and one current image 35, 46, or 49 are respectively displayed side by side on the past image region 32, 40, or 43 and the current image region 33, 41, and 44. However, a plurality of past images and a plurality of current images may be displayed side by side on a past image region and a current image region, respectively. A second display screen 50 illustrated in an example of FIG. 15 has the past image region 32 and the current image region 33 that are displayed adjacent to each other left and right. Additionally, two past images 51 and 52 in addition to the past image 34 are further displayed side by side above and below the past image 34 on the past image region 32, and, one current image 53 in addition to the current image 35 is further displayed above the current image 35 on the current image region 33. Although the past image 51 displayed above the past image 34 is not illustrated, the past image 51 is a past image located one position before the past image 34 corresponding to the current image 35 newly created in the ultrasound diagnostic device in the arrangement order of the past image group in which the first display is performed. Additionally, the past image 52 displayed below the past image 34 is a past image located one position after a past image, in the arrangement order of the past image group in which the first display is performed. Additionally, the current image 53 displayed above the current image 35 is a current image created in correspondence with the past image 51 displayed above the past image 34 in the current routine test.

Figure 15:
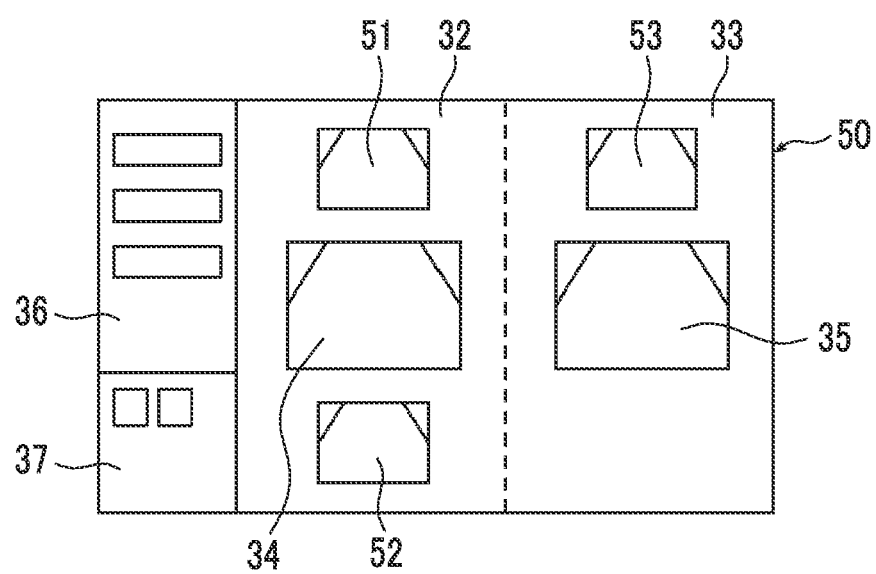
FIG. 15 is a conceptual diagram of an example illustrating a screen including the second display in Embodiment 4.

In addition, Embodiment 4 illustrated in FIG. 15 has the same configuration as Embodiment 1 illustrated in FIGS. 1 to 11 except for the second display screen 50, the past images 51 and 52, and the current image 53. For that reason, in the following, in FIG. 15, the same constituent elements as FIG. 11 will be designated by the same reference signs, and the detailed description of the constituent elements will be omitted.

As illustrated in FIG. 15, after the current image 35 corresponding to the past image 34 is displayed on the current image region 33 in the second display screen 50, for example, the second current display can be made to transition to the next second display by canceling freeze of display of a frozen diagnostic-device-side display unit in order to determine an ultrasound image to be saved, though not illustrated. In that case, in the past image region 32, the past image 51 is not displayed, the past images 34 and 52 move upward one by one and displayed, and the next past image of the past image 52 in the past image group subjected to the first display time is displayed below on the past image 52. That is, the past image 34 is displayed on the display position of the past image 51 of FIG. 15, and the past image 52 is displayed on the display position of the past image 34 of FIG. 15. Additionally, in the current image region 33, the current image 35 is displayed on the display position of the current image 53 of FIG. 15, a portion below the current image 35 is brought into a blank state, and then, a current image corresponding to the past image 52 is displayed as soon as an ultrasound image that is newly created is saved is determined.

In addition, as illustrated in FIG. 15, since the current image corresponding to the past image 52 displayed below the past image 34 is not created at the present time, the current image is not displayed on the current image region 33. Additionally, in order to emphasize the past image 34 corresponding to a part under diagnosis at the present time and the current image 35 corresponding to the past image 34, the past images 51 and 52 displayed above and below of the past image 34 and the current image 53 displayed above on the current image 35 may be displayed to be smaller than the past image 34 and the current image 35.

Figure 16:
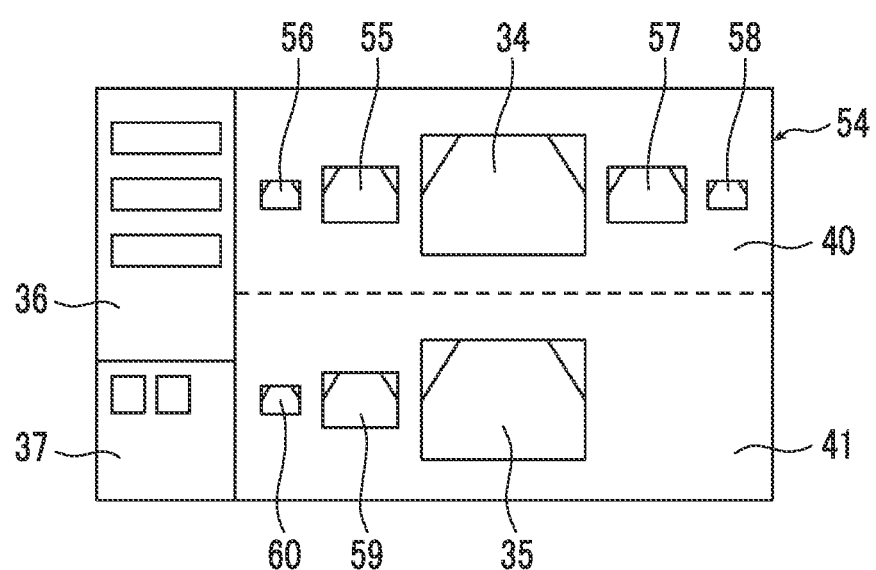
FIG. 16 is a conceptual diagram of another example illustrating the screen including the second display in Embodiment 4.

Additionally, a modification example of the present embodiment is illustrated in FIG. 16. An aspect illustrated in FIG. 16 is different from an aspect in FIG. 15 in terms of only a second display screen 54. In the example illustrated in FIG. 16, the second display screen 54 has the past image region 40 and the current image region 41 that are displayed adjacent to each other up and down and. Although not illustrated, four past images 55, 56, 57, and 58 in addition to the past image 34 are displayed side by side on the left and right of the past image 34 in the arrangement order of the past image group in the first display on the past image region 40. Here, the past image 34 is an ultrasound image corresponding to the ultrasound image newly created at the present time, and the past image 55 displayed adjacent to the left side of the past image 34 is a past image located one position before the past image 34 in the arrangement order of the past image group in which the first display is performed. Additionally, the past image 56 of the past image 55 displayed further adjacent to the left side is a past image located two positions before the past image 34 in the arrangement order of the past image group in which the first display is performed. Additionally, the past image 57 displayed adjacent to the right side of the past image 34 is a past image located one location after the past image 34 in the arrangement order of the past images in which the first display is performed. Additionally, the past image 58 of the past image 57 displayed further adjacent to the right side is a past image located two positions after the past image 34 in the arrangement order of the past image group in which the first display is performed. Additionally, the current image 59 displayed adjacent to the left side of the current image 35 is a current image created in correspondence with the past image 55 in the current routine test, and the current image 60 of the current image 59 displayed further adjacent to the left side is a current image created in correspondence with the past image 56. Additionally, in order to emphasize the past image 34 corresponding to a part under diagnosis at the present time and the current image 35 corresponding to the past image 34, the past images 55, 56, 57, and 58 and the current images 59 and 60 may be displayed to be smaller than the past image 34 and the current image 35. Moreover, in order to emphasize the arrangement order of the past image group in the first display, the past image 56 adjacent to the left side of the past image 55 may be displayed to be smaller than the past image 55, and the past image 58 further adjacent to the right side than the past image 57 may be displayed to be smaller than the past image 57, and the current image 60 further adjacent to the left side the current image 59 may be displayed to be smaller than the current image 59.

In the above configuration, one or more past images displayed before and after one past image in the arrangement order of the first display are arranged on both sides of the one past image 34 displayed on the past image regions 32 and 39 in the second display and are displayed to be smaller than the one past image 34. Additionally, one or more ultrasound images including the ultrasound image created immediately before the current image 35 in the current routine test are displayed to be smaller than the current image 35 on one side of the current image 35 displayed on the current image regions 33 and 40 in the second display in correspondence with the one past image 34. By performing the second display in this way, the operator can perform the ultrasound diagnosis while checking diagnosis parts before and after the current ultrasound diagnosis. Additionally the operator can check an ultrasound image newly created during the ultrasound diagnosis and an ultrasound image created before the newly created ultrasound image.

Embodiment 5

In the second display of Embodiments 1 to 4 illustrated in FIGS. 7 and 10 to 16, although one past image 34, 45, or 48 and the current image 35, 46, or 49 corresponding to the one past image are displayed side by side on the past image region 32, 40, or 43 and the current image region 33, 41, or 44, thumbnail list display of a plurality of past images and a plurality of current images may be performed on the past image region 32, 40, or 43 and the current image region 33, 41, or 44.

Figure 17:
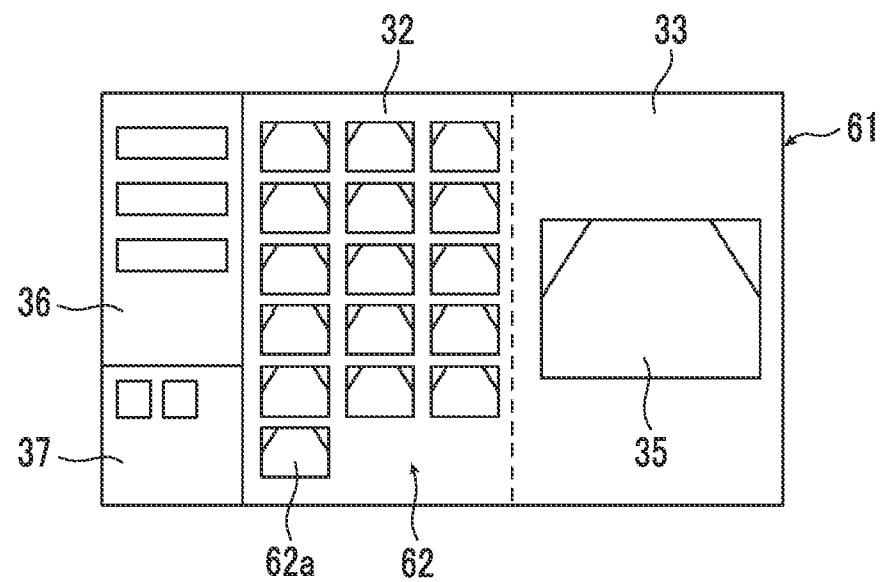
FIG. 17 is a conceptual diagram of an example illustrating a screen including the second display in Embodiment 5.

In addition, Embodiment 5 illustrated in FIG. 17 has the same configuration as Embodiment 1 illustrated in FIGS. 1 to 11 except that the past image group 62 displayed as thumbnails on the past image region 32 of a second display screen 61. Additionally, a modification example of Embodiment 5 illustrated in FIG. 18 has the same configuration as Embodiment 1 illustrated in FIGS. 1 to 11 except that a past image group 62 and a current image group 65 displayed as thumbnails on the past image region 32 and the current image region 33 of a second display screen 63. For that reason, in the following, in FIGS. 17 and 18, the same constituent elements as FIG. 11 will be designated by the same reference signs, and the detailed description of the constituent elements will be omitted.

The past image group 62 constituted of past images 62*a* is displayed as a thumbnail list on the past image region 32 of the second display screen 61 illustrated in FIG. 17, and the current image 35 after a current image corresponding to a past image at the rearmost end of the past image group 62 is created is displayed on the current image region 33. That is, in a case where an ultrasound image is further captured after all the ultrasound images corresponding to the past image group 62 are captured, the past image group 62 may be displayed as a thumbnail list instead of displaying one past image on the past image region 32.

Figure 18:
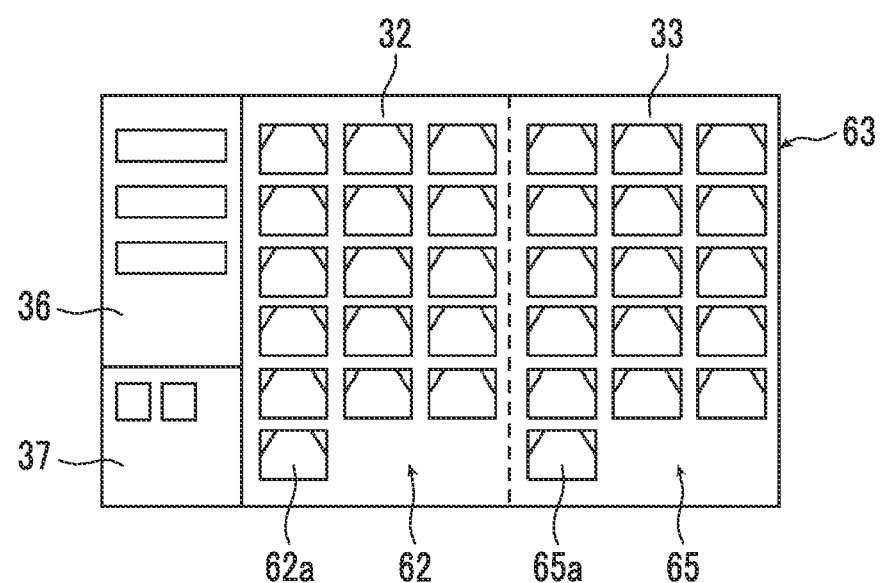
FIG. 18 is a conceptual diagram of another example illustrating the screen including the second display in Embodiment 5.

Additionally, in a case where the capturing of the ultrasound image is completed, as in a modification example of the present embodiment illustrated in FIG. 18, the current image group 65 constituted of current images 65*a* that are ultrasound images captured in the current routine test may be displayed on the current image region 33 of the second display screen 63. In addition, in the current ultrasound diagnosis, in a case where an ultrasound image is further captured after all the ultrasound images corresponding to the respective past images of the past image group 62 are captured, the ultrasound image may be displayed as a thumbnail at the rearmost end of the current image group 65. In addition, in the examples illustrated in FIGS. 17 and 18, the past image region 32 and the current image region 33 are displayed adjacent to each other left and right. However, it is needless to say that these past and current image regions may be displayed adjacent to each other up and down as in Embodiment 2 illustrated in FIG. 12.

As described above, by displaying the past image group 62 corresponding to the current routine test only on the past image region 32 in the second display, the operator can check that the currently performed ultrasound diagnosis is out of the routine test, and can perform the ultrasound diagnosis while checking the past image group 62. Additionally, in a case where the routine test is completed, the past image group 62 and the current image group 65 are displayed side by side on the past image region 32 and the current image region 33. Accordingly, the operator can compare the past image group 62 with the current image group 65 to finally check the plurality of ultrasound images captured at this time.

Embodiment 6

In the second display of Embodiments 1 to 4 illustrated in FIGS. 7 and 10 to 16, one past image 34, 45, or 48 that is an ultrasound image captured in a past routine test is displayed on the past image region 32, 40, or 43. However, images other than the image of the past routine test may be displayed on the past image region.

Figure 19:
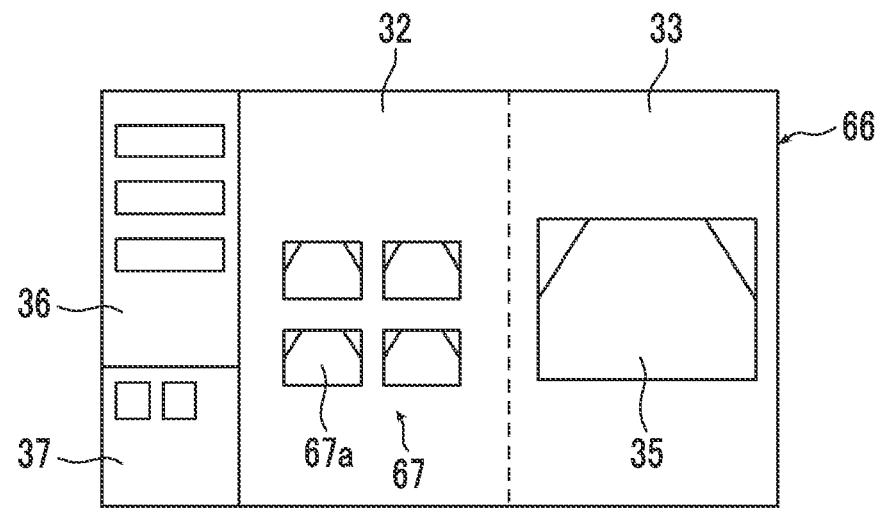
FIG. 19 is a conceptual diagram of an example illustrating a screen including the second display in Embodiment 6.

In addition, Embodiment 6 illustrated in FIG. 19 has the same configuration as Embodiment 1 illustrated in FIGS. 1 to 11 except that a selected image group 67 selected by the operator is displayed on the past image region 32 of a second display screen 66. Additionally, a modification example of Embodiment 6 illustrated in FIG. 20 has a past image region 69 and a current image region 70 of a second display screen 68 and has the same configuration as Embodiment 1 illustrated in FIGS. 1 to 11 except that the past image 34 and a selected image 71 are displayed on the past image region 69. For that reason, in the following, in FIGS. 19 and 20, the same constituent elements as FIG. 11 will be designated by the same reference signs, and the detailed description of the constituent elements will be omitted.

In the example illustrated in FIG. 19, the selected image group 67 constituted of selected images 67*a* selected by the operator is displayed on the past image region 32 of the second display screen 66. Although not illustrated, the selected image group 67 is images selected by the operator via the input unit of the workstation among the plurality of images stored in the workstation-side storage unit. Additionally the selected images 67*a* may be medical images, such as endoscopic images, radiological images, and diagnostic images obtained using magnetic resonance imaging (MRI) in addition to the ultrasound images, or a plurality of types of medical images may be included in a case where a plurality of selected images are selected. Moreover, the selected images 67*a* may be selected at least before the operator starts the screening test. For example, one or more selected images selected as selected images by the operator after the previous routine test may be selected together with a past image group to be referred to in the current ultrasound diagnosis in the screen of the workstation-side display unit as illustrated in FIG. 8. Additionally, for example, in the screen of the workstation-side display unit as illustrated in FIG. 8, the selected images may be selected by the operator and may be selected together with the past image group to be referred to in the current ultrasound diagnosis.

Meanwhile, there is a case where the operator generates a test report using the ultrasound images acquired in the routine test after the end of the routine test. Although not illustrated, the test report may be electronic data generated using the workstation after the end of the routine test. In that case, for example, the test report is generated in the workstation-side control unit, using data, such as text data input by the operator via the input unit and layout information on images, and the ultrasound images stored in the workstation-side storage unit, and is stored in the workstation-side storage unit.

In this case, a report generation screen for allowing the operator to create the test report may be displayed in the workstation-side display unit. The ultrasound images attached to the test report generated in this way may be selected by the operator for each test report as the selected images 67a illustrated in FIG. 19. In addition, medical images, such as endoscopic images, the radiological images, and diagnostic images using MRI, which are acquired in the past, in addition to the ultrasound images acquired in the routine test, may be attached to the test report, and the medical images may be selected as the selected images 67a for each test report by the operator.

One or more past images selected in this way are displayed on the past image region 32 of the second display screen 66 illustrated in FIG. 19 after the second display of the respective past images of the past routine tests selected together with the selected images is performed. In addition, the selected images displayed on the past image region 32 may be sequentially displayed on the past image region 32 in operator's selection order, using a plurality of images as one set as the selected image group 67, as illustrated in the example of FIG. 19, or the selected images may be sequentially displayed on the past image region 32 in operator's selection order one by one. Additionally, although not illustrated, the selected images selected by the operator may be displayed as thumbnails in the first display after the rearmost end of the past routine tests that are displayed as a thumbnail list. In that case, the arrangement order of one or more selected images may be set by the operator via the input unit of the workstation or may be time-series order in which the respective selected images are created.

Additionally, the selected images may be displayed in association with the respective past images that constitute the past image group in the past routine tests. In the example illustrated in FIG. 20, the second display screen 68 has the past image region 69 that is an enlarged region and the current image region 70 that is reduced by the amount of enlargement of the past image region 69, and the past image 34 and the selected image 71 are displayed adjacent to the past image region 69. Although not illustrated, for example in a case where the selected image 71 is selected by the operator via the input unit of the workstation together with the past image group of the past routine tests, setting indicating that the second display is performed together with the past image 34 may be performed. Additionally, although not illustrated, for example, the workstation-side display control unit may be controlled such that a selected image associated with one past image is subjected to the second display together with the past image. In that case, in a case where the selected image 71 is selected by the operator via the input unit of the workstation, setting indicating that the past image 34 and the selected image 71 are associated with each other may be performed. Additionally, although not illustrated, the workstation-side control unit may be controlled so as to automatically associate diagnostic images of the same part of a past routine test corresponding to the past routine test including the past image 34 with each other.

Figure 20:
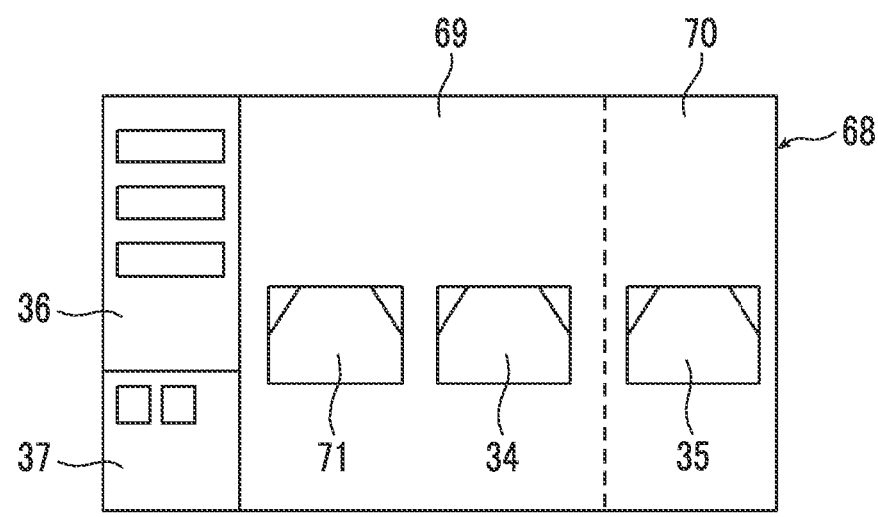
FIG. 20 is a conceptual diagram of another example illustrating the screen including the second display in Embodiment 6.

In addition, in the examples illustrated in FIGS. 19 and 20, the past image region 32 or 69 and the current image region 33 or 70 are displayed adjacent to each other left and right. However, it is needless to say that these past and current image regions may be displayed adjacent to each other up and down as in Embodiment 2 illustrated in FIG. 12.

Additionally, the selected image may be a moving image. Although not illustrated, the moving image is a moving image saved in the temporary memory, for example, in a case where the display of the diagnostic-device-side display unit of the ultrasound diagnostic device is frozen in a past routine test. Additionally, the moving image may be stored in the workstation-side storage unit via the diagnostic-device-side information transmission unit and the workstation-side information transmission unit together with ultrasound images that include the moving image as still images and are determined as the saved data. In a case where the moving image is used as the selected image, respective past images may be replaced with corresponding moving images, respectively. In that case, the moving images may be sequentially reproduced in a loop in the arrangement order of the first display in the past image region 32 in the second display.

Additionally, although not illustrated, the selected image may be element data before image processing, which is output from the receiving circuit of the ultrasound diagnostic device. In this way, in a case where a plurality of types of image data and moving image data are included as selected images and the plurality of selected images are subjected to the first display and sequentially the second display together with a past image group for past routine tests, the arrangement order and the display order thereof may be set via the input unit or the like of the workstation. That is, for example, the arrangement order and the display order of the past image group and the plurality of selected images may be time-series order in which the plurality of past images constituting the past image group, and the plurality of selected images are created, or may be the order of image types. Here, the order of image types is, for example, order in which ordering is performed in accordance with to the types of images such that, among a plurality of types of data, still images are first arranged and displayed, then moving images are arranged and displayed, and then element data before image processing are arranged and displayed. Additionally, tag information (DICOM tags) specified in Digital Imaging and Communication in Medicine (DICOM) that is a standard, such as a format of medical images, is often embedded in medical image data, such as the ultrasound images. The DICOM tags, for example, represents diagnosis parts, such as the carotid artery and the thyroid gland in the ultrasound diagnosis, and ordering may be performed on the DICOM tags and the past image group and the plurality of selected images may be arranged and displayed on the basis of that order. The ordering of the DICOM tags may be, for example, set by the operator via the input unit of the workstation.

As described above, the operator can perform the ultrasound diagnosis by displaying the selected image group 67 or the selected images 67a and 71 selected by the operator on the past image regions 32 and 69, referring to images other than the past images. Additionally, the operator can perform ultrasound diagnosis of other parts that the operator wants to diagnose, referring to appropriate images, in addition to the ultrasound diagnosis corresponding to the past routine tests. Moreover, in a case where moving images of past routine tests are used as selected images, the operator can check ultrasound diagnosis in the past routine tests in detail.

Although the ultrasound diagnostic system related to the embodiment of the invention have been described above in detail, it is natural that the invention is not limited to the above examples, and various improvements and modifications may be made without departing from the scope of the invention. Additionally, the plurality of embodiments and examples that are shown above can be appropriately used in combination.

EXPLANATION OF REFERENCES

1: ultrasound diagnostic system
2: ultrasound diagnostic device
3: workstation
4: array transducer
5: transmitting circuit
6: receiving circuit
7: image creation unit
8: temporary memory
9: diagnostic-device-side display control unit
10: diagnostic-device-side display unit
11: saved data determination unit
12: diagnostic-device-side information transmission unit
13: diagnostic-device-side control unit
14: diagnostic-device-side operating unit
15: diagnostic-device-side storage unit
16: workstation-side information transmission unit
17: workstation-side display control unit
18: workstation-side display unit
19: time setting unit
20: workstation-side control unit
21: workstation-side storage unit
22: input unit
23: amplification unit
24: AD conversion unit
25: signal processing unit
26: DSC
27: image processing unit
28: first display screen
29: thumbnail image display region
30, 62: past image group
30a, 34, 45, 48, 51, 52, 55, 56, 57, 58, 62a: past image
31, 38, 39, 42, 47, 50, 54, 61, 63, 66, 68: second display screen
32, 40, 43, 69: past image region
33, 41, 44, 70: current image region
35, 46, 49, 53, 59, 60, 65a: current image
36: information display input region
37: list display selection region
65: current image group
67: selected image group
67a, 71: selected image

What is claimed is:

1. An ultrasound diagnostic system including an ultrasound diagnostic device that transmits an ultrasound beam toward a subject from an array transducer, and receives an ultrasound echo from the subject to create a plurality of ultrasound images, and a workstation connected to the ultrasound diagnostic device, the ultrasound diagnostic system comprising:
a storage unit configured to store a plurality of ultrasound images in past diagnosis of a plurality of subjects as past images,
wherein the ultrasound diagnostic device has
a diagnostic device side processor configured to determine a current image that is the ultrasound image to be stored to the storage unit among moving image data made of the plurality of ultrasound images created in a current diagnosis,
wherein the workstation has
an input unit for allowing an operator to input various kinds of information,
a workstation-side display unit, and
a workstation-side processor configured to control display in the workstation-side display unit, and
wherein, in a case where a routine test in which a plurality of parts of the subject are sequentially subjected to ultrasound diagnosis in accordance with a determined procedure is performed and in a case where information on the subject is input from the input unit,
the workstation-side processor is configured to
make the workstation-side display unit perform a first display in which a plurality of past images in a past routine test of the subject stored in the storage unit are displayed as a thumbnail list and then perform a second display in which one past image and the current image which is determined in the ultrasound diagnostic device with respect to a part corresponding to the one past image are displayed side by side on a past image region and a current image region adjacent to each other, in an arrangement order of the plurality of past images displayed as the thumbnail list in the first display,
make the workstation-side display unit display a next past image in the arrangement order of the first display on the past image region in the second display after the second display of the current image corresponding to the one past image is performed, and
make the current image region blank until a current image corresponding to the next past image is determined by the ultrasound diagnostic device and displayed on the current image region from a time point when the next past image is displayed on the past image region,
each time a display in the past image region is updated according to the arrangement order, the blank and a current image corresponding to a past image being displayed in the past image region, are displayed alternately in the current image region.

2. The ultrasound diagnostic system according to claim 1, wherein the workstation-side processor is further configured to
set a transition time taken until the first display of the workstation-side display unit transitions to the second display, and
make the display in the workstation-side display unit automatically transition from the first display to the second display after elapse of the transition time from a time point when the first display is performed.

3. The ultrasound diagnostic system according to claim 2, wherein the workstation-side processor is further configured to set a set time input by the operator via the input unit as the transition time.

4. The ultrasound diagnostic system according to claim 2, wherein the workstation-side processor is further configured to determine the transition time based on a plurality of the transition times in a plurality of times of past ultrasound diagnosis.

5. The ultrasound diagnostic system according to claim 1, wherein the ultrasound diagnostic device has an ultrasound diagnostic device-side processor configured to set a transition time taken until the first display of the workstation-side display unit transitions to the second display, and wherein the ultrasound diagnostic device-side processor is further configured to make the display in the workstation-side display unit automatically transition from the first display to the second display after elapse of the transition time from a time point when the first display is performed.

6. The ultrasound diagnostic system according to claim 5, wherein the ultrasound diagnostic device-side processor is further configured to set a set time input by the operator via the input unit as the transition time.

7. The ultrasound diagnostic system according to claim 5, wherein the ultrasound diagnostic device-side processor is further configured to determine the transition time based on a plurality of the transition times in a plurality of times of past ultrasound diagnosis.

8. The ultrasound diagnostic system according to claim 1, wherein, in a case where information indicating that the transition time taken until the first display transitions to the second display is changed is input by the operator via the input unit, the workstation-side processor is configured to shorten or extend a time taken for transition from a time point during the first display to the second display in the workstation-side display unit.

9. The ultrasound diagnostic system according to claim 2, wherein, in a case where information indicating that the transition time taken until the first display transitions to the second display is changed is input by the operator via the input unit, the workstation-side processor is further configured to shorten or extend a time taken for transition from a time point during the first display to the second display in the workstation-side display unit.

10. The ultrasound diagnostic system according to claim 4, wherein, in a case where information indicating that the transition time taken until the first display transitions to the second display is changed is input by the operator via the input unit, the workstation-side processor is configured to shorten or extend a time taken for transition from a time point during the first display to the second display in the workstation-side display unit.

11. The ultrasound diagnostic system according to claim 1, wherein, in a case where information indicating that the second display is made to transition to the first display is input by the operator via the input unit, the workstation-side processor is further configured to make the second display in the workstation-side display unit transition to the first display.

12. The ultrasound diagnostic system according to claim 2, wherein, in a case where information indicating that the second display is made to transition to the first display is input by the operator via the input unit, the workstation-side processor is configured to make the second display in the workstation-side display unit transition to the first display.

13. The ultrasound diagnostic system according to claim 1, wherein the workstation-side processor is further configured to make the workstation-side display unit display past images displayed before and after the one past image in the arrangement order of the first display, side by side on both sides of the one past image displayed on the past image region in the second display, so as to be smaller than the one past image.

14. The ultrasound diagnostic system according to claim 13, wherein the workstation-side processor is further configured to make the workstation-side display unit display an ultrasound image created immediately before the current image in a current routine test, on one side of the current image displayed on the current image region in the second display in correspondence with the one past image, so as to be smaller than the current image.

15. The ultrasound diagnostic system according to claim 1, wherein the workstation-side processor is further configured to make the workstation-side display unit display the past image in the second display on the past image region so as to be larger than the current image displayed on the current image region.

16. The ultrasound diagnostic system according to claim 1, wherein the workstation-side processor is further configured to make the workstation-side display unit display the past image region and the current image region in the second display adjacent to each other left and right or up and down and display the past image and the current image side by side.

17. The ultrasound diagnostic system according to claim 1, wherein the workstation-side processor is further configured to make the workstation-side display unit display the plurality of past images as the thumbnail list on the past image region and display a plurality of current images created in a current routine test as a thumbnail list on the current image region after a last past image in the arrangement order of the first display and a current image corresponding to the last past image are displayed on the past image region and the current image region in the second display.

18. The ultrasound diagnostic system according to claim 1, wherein the workstation-side control unit is further configured to make the workstation-side display unit display at least one or more selected images selected based on information indicating that images input by the operator via the input unit are selected, as a thumbnail list at a rearmost end of the plurality of past images in the arrangement order of the first display, and display the one or more selected images subsequent to the plurality of past images on the past image region in the second display.

19. A method of controlling an ultrasound diagnostic system including an ultrasound diagnostic device that transmits an ultrasound beam toward a subject from an array transducer, and receives an ultrasound echo from the subject to create a plurality of ultrasound images, and a workstation connected to the ultrasound diagnostic device, the method comprising:

storing a plurality of ultrasound images in past diagnosis of a plurality of subjects as past images;

determining a current image that is the ultrasound image to be stored among moving image data made of the plurality of ultrasound images created in a current diagnosis; and in a case where a routine test in which a plurality of parts of the subject are sequentially subjected to ultrasound diagnosis in accordance with a determined procedure is performed, and in a case where information on the subject is input, making a workstation-side display unit of the workstation perform a first display in which a plurality of past images in a past routine test of the subject that are stored are displayed as a thumbnail list and then perform a second display in which one past image and a current image which is determined in the ultrasound diagnostic device with respect to a part corresponding to the one past image are displayed side by side on a past image region and a current image region adjacent to each other, in an arrangement order of the plurality of past images displayed as the thumbnail list in the first display, making the workstation-side display unit display a next past image in the arrangement order of the first display on the past image region in the second display after the second display of the current image corresponding to the one past image is performed, and making the current image region blank until a current image corresponding to the next past image is determined by the ultrasound diagnostic device and displayed on the current image region from a time point when the next past image is displayed on the past image region, each time a display in the past image region is updated according to the arrangement order, the blank and a current image corresponding to a past image being displayed in the past image region, are displayed alternately in the current image region.

* * * * *